(12) United States Patent
Mickle et al.

(10) Patent No.: US 10,144,740 B2
(45) Date of Patent: Dec. 4, 2018

(54) BENZOIC ACID, BENZOIC ACID DERIVATIVES AND HETEROARYL CARBOXYLIC ACID CONJUGATES OF OXYCODONE, PRODRUGS, METHODS OF MAKING AND USE THEREOF

(71) Applicant: KemPharm, Inc, Coralville, IA (US)

(72) Inventors: Travis Mickle, Kissimmee, FL (US); Sven Guenther, Coralville, IA (US); Sanjib Bera, Blacksburg, VA (US); Bindu Bera, Blacksburg, VA (US); Jaroslaw Kanski, Blacksburg, VA (US); Andrea Martin, Fincastle, VA (US)

(73) Assignee: KemPharm, Inc., Coralville, IA (US)

( * ) Notice: Subject to any disclaimer, the term of this patent is extended or adjusted under 35 U.S.C. 154(b) by 0 days.

(21) Appl. No.: 15/812,730

(22) Filed: Nov. 14, 2017

(65) Prior Publication Data

US 2018/0065975 A1   Mar. 8, 2018

Related U.S. Application Data

(63) Continuation of application No. 14/952,348, filed on Nov. 25, 2015, now Pat. No. 9,850,252.

(60) Provisional application No. 62/084,246, filed on Nov. 25, 2014, provisional application No. 62/084,216, filed on Nov. 25, 2014.

(51) Int. Cl.
*C07D 489/04* (2006.01)
*C07D 498/08* (2006.01)
*A61P 25/36* (2006.01)

(52) U.S. Cl.
CPC ............ *C07D 489/04* (2013.01); *A61P 25/36* (2018.01); *C07D 498/08* (2013.01)

(58) Field of Classification Search
CPC ...... C07D 489/04; C07D 498/08; A61P 25/36
See application file for complete search history.

(56) References Cited

U.S. PATENT DOCUMENTS

| | | | |
|---|---|---|---|
| 1,731,152 | A | 10/1929 | Schopf |
| 4,668,685 | A | 5/1987 | Shami |
| 7,375,082 | B2 | 5/2008 | Mickle et al. |
| 7,375,083 | B2 | 5/2008 | Mickle et al. |
| 8,461,137 | B2 | 6/2013 | Mickle et al. |
| 8,748,413 | B2 | 6/2014 | Mickle et al. |
| 8,759,368 | B2 | 6/2014 | Mickle et al. |
| 8,828,978 | B2 | 9/2014 | Mickle et al. |
| 8,871,780 | B2 | 10/2014 | Mickle et al. |
| 8,927,716 | B2 | 1/2015 | Mickle et al. |
| 9,125,947 | B2 | 9/2015 | Mickle et al. |
| 9,132,125 | B2 | 9/2015 | Mickle et al. |
| 9,650,387 | B2 | 5/2017 | Mickle et al. |
| 9,850,252 | B2 | 12/2017 | Mickle et al. |
| 2004/0058946 | A1 | 3/2004 | Buchwald et al. |
| 2004/0180036 | A1 | 9/2004 | Ashton et al. |
| 2004/0204025 | A1 | 10/2004 | Shafer et al. |
| 2004/0254182 | A1 | 12/2004 | Mulvihill et al. |
| 2005/0074493 | A1 | 4/2005 | Mehta et al. |
| 2005/0080012 | A1 | 4/2005 | Mickle et al. |
| 2005/0176646 | A1 | 8/2005 | Mickle et al. |
| 2005/0203115 | A1 | 9/2005 | Sancilio et al. |
| 2006/0167258 | A1 | 7/2006 | Likhotovorik et al. |
| 2008/0090771 | A1 | 4/2008 | Moncrief |
| 2008/0132570 | A1 | 6/2008 | Xiang et al. |
| 2009/0156820 | A1 | 6/2009 | Wang et al. |
| 2011/0002990 | A1 | 1/2011 | Mickle et al. |
| 2011/0002991 | A1 | 1/2011 | Mickle et al. |
| 2011/0040072 | A1* | 2/2011 | Mickle ............... A61K 9/0019 530/330 |
| 2012/0142719 | A1* | 6/2012 | Mickle ............... A61K 31/485 514/282 |
| 2012/0142720 | A1 | 6/2012 | Mickle et al. |
| 2013/0245265 | A1 | 9/2013 | Mickle et al. |
| 2013/0252994 | A1 | 9/2013 | Mickle et al. |
| 2013/0259909 | A1 | 10/2013 | Mickle et al. |
| 2014/0330021 | A1 | 11/2014 | Mickle et al. |
| 2015/0065536 | A1 | 3/2015 | Mickle et al. |

(Continued)

FOREIGN PATENT DOCUMENTS

| | | |
|---|---|---|
| AT | 229496 | 9/1963 |
| EA | 008864 | 8/2007 |

(Continued)

OTHER PUBLICATIONS

Bertram, F. and W. Stoltenberg, "Klinische Erfahrungen Mit Acedicon," Klinische Wochenschrift, 8, Jahrgang, Nov. 19, 1929, pp. 883-886.
Bradford, L.W. and J.W. Brackett, "Systematic Procedure for the Identification of Dangerous Drugs, Poisons, and Narcotics by Ultraviolet Spectrophotometry," Laboratory of Criminalistics, 1956, pp. 353-382.
Caitlin et al., "Analytical Chemistry at the Games of the XXIIIrd Olympiad in Los Angeles, 1984," Clinical Chemistry, vol. 33, No. 2, 1987, pp. 319-327.
Fischer, R. and M.S. Karawia, "Zum Nachweis von Analgeticis und Alkaloiden Mittels Tetraphenylbornatrium (Kalignost) und Nitrokorpern," Aus dem Pharmakognostischen Institut der Universitat Graz, 1953, pp. 366-374.

(Continued)

*Primary Examiner* — Dennis Heyer
*Assistant Examiner* — Daniel M Podgorski
(74) *Attorney, Agent, or Firm* — Robert Hoag; McAndrews, Held & Malloy, Ltd.

(57) ABSTRACT

The presently described technology provides compositions comprising aryl carboxylic acids and, for example NSAIDs, chemically conjugated to oxycodone (4,5-α-epoxy-14-hydroxy-17-methylmorphinan-6-one) to form novel prodrugs/compositions of oxycodone, including benzoates, salicylates, propionates, fenamates, and acetates, which have a decreased potential for abuse of oxycodone. The present technology also provides methods of treating patients, pharmaceutical kits and methods of synthesizing conjugates of the present technology.

17 Claims, 30 Drawing Sheets

(56) References Cited

U.S. PATENT DOCUMENTS

| | | | |
|---|---|---|---|
| 2016/0168160 A1 | 6/2016 | Mickle et al. | |
| 2017/0143696 A1 | 5/2017 | Mickle et al. | |
| 2017/0226118 A1 | 8/2017 | Mickle et al. | |

FOREIGN PATENT DOCUMENTS

| | | |
|---|---|---|
| EP | 1782834 | 5/2007 |
| GB | 320749 | 10/1929 |
| WO | 9208459 | 5/1992 |
| WO | 9616063 | 5/1996 |
| WO | 9902529 | 1/1999 |
| WO | 02098427 | 12/2002 |
| WO | 2005032474 | 4/2005 |
| WO | 2007140272 | 12/2007 |
| WO | 2011002991 | 1/2011 |
| WO | 2011002995 | 1/2011 |
| WO | 2011008636 | 1/2011 |
| WO | 2012096887 | 7/2012 |

OTHER PUBLICATIONS

Hosztafi, S., Köhegyi, I., Simon, C., Fürst, Z., "Synthesis and Analgetic Activity of Nicotinic Esters of Morphine Derivatives," Arzneimittel-Forschung [1993, 43(11):1200-1203].
Hydrocodone chemical structure (ChemSpider, last visit Sep. 18, 2013).
Jane, I., A. McKinnon, and R.J. Flanagan, "High-Performance Liquid Chromatographic Analysis of Basic Drugs on Silica Columns Using Non-Aqueous Ionic Eluents. II. Application of UV, Fluorescence and Electrochemical Oxidation Detection," Journal of Chromatography, 323, 1985, pp. 191-225.
Leland, D.L., J.O. Polazzi and M.P. Kotick, "Preparation of 7-beta-Methyldihydrothebaine," J. Org . Chem., 45, 1980, pp. 4026-4028.
Micheel, F. and W. Leifels, "Papierchromatographische Trennungen von Alkaloidgemischen an Succinylzellulose-Papieren," Aus dem Organisch-chemischen Institut der Universitat Munster i. W., 1960.
Perrigo et al., "Use of Dual-Column Fused-Silica Capillary Gas Chromatography in Combination with Detector Response Factors for Analytical Toxicology," Journal of Chromatography, 341, 1985, pp. 81-88.
Persson-Stubberud, Karin and Astrom, Ove, "Separation of ibuprofen, codeine phosphate, their degradation products and impurities by capillary electrophoresis I. Method development and optimization with fractional factorial design," Journal of Chromatography A, 798 (1998) pp. 307-314.
Small, L., H.M. Fitch and W.E. Smith, "The Addition of Organomagnesium Halides to Pseudocodeine Types. II. Preparation of Nuclear Alkylated Morphine Derivatives," Preparation of Nuclear Alkylated Morphine Derivatives, J. Am. Chem. Soc., Aug. 1936, pp. 1457-1463.
Small, L., S. G. Turnbull, and H.M. Fitch, "The Addition of Organomagnesium Halides to Pseudocodeine Types. IV. Nuclear-Substituted Morphine Derivatives," J. Org. Chem., 1938, pp. 204-232.
Thebacon—List of Thebacon suppliers; SciFinder Scholar, Report for CAS RN 466-90-0, 2011.
Von Ernst Vidic, "Eine neue Schnellmethode zur Untersuchung von Urin auf Opiate und deren Derivate," Aus dem Institut fur gerichtliche und soziale Medizin der Freien Universitat Berlin, 1951.
International Search Report in PCT/US2010/040775, dated Aug. 16, 2010.
International Search Report in PCT/US2010/040785, dated Aug. 20, 2010.
Office Action in U.S. Appl. No. 12/828,381, dated Aug. 1, 2012.
Office Action in U.S. Appl. No. 12/828,456, dated Aug. 21, 2012.
Office Action in U.S. Appl. No. 12/828,381, dated Nov. 8, 2012.
Office Action in U.S. Appl. No. 12/828,456, dated Dec. 19, 2012.
Office Action in U.S. Appl. No. 12/828,456, dated Feb. 6, 2013.
Office Action in U.S. Appl. No. 13/378,857, dated Feb. 22, 2013.
Notice of Allowance in U.S. Appl. No. 12/828,381, dated Mar. 25, 2013.
Office Action in U.S. Appl. No. 13/378,857, dated May 23, 2013.
Office Action in U.S. Appl. No. 13/888,578, dated Jul. 2, 2013.
Notice of Allowance in U.S. Appl. No. 12/828,456, dated Jul. 24, 2013.
Office Action in U.S. Appl. No. 13/888,583, dated Aug. 2, 2013.
Notice of Allowance in U.S. Appl. No. 13/888,578, dated Sep. 4, 2013.
Office Action in U.S. Appl. No. 13/378,800, dated Sep. 19, 2013.
Office Action in U.S. Appl. No. 13/378,857, dated Sep. 25, 2013.
Notice of Allowance in U.S. Appl. No. 13/888,578, dated Feb. 10, 2014.
Notice of Allowance in U.S. Appl. No. 13/378,800, dated Mar. 6, 2014.
Notice of Allowance in U.S. Appl. No. 13/888,583, dated May 2, 2014.
Notice of Allowance in U.S. Appl. No. 12/828,456, dated Jul. 22, 2014.
Notice of Allowance in U.S. Appl. No. 13/888,587, dated Sep. 12, 2014.
Office Action in U.S. Appl. No. 14/493,611, dated Dec. 16, 2014.
Office Action in U.S. Appl. No. 14/557,570, dated Jan. 30, 2015.
Notice of Allowance in U.S. Appl. No. 14/493,611, dated Mar. 24, 2015.
Notice of Allowance in U.S. Appl. No. 14/557,570, dated Apr. 14, 2015.
Notice of Allowance in U.S. Appl. No. 14/557,570, dated May 4, 2015.
Notice of Allowance in U.S. Appl. No. 14/493,611, dated Apr. 30, 2015.
Corrected Notice of Allowance in U.S. Appl. No. 14/493,611, dated Jul. 30, 2015.
EP Search Report for Appl. No. 10 794 765.7 dated May 6, 2015.
European Patent Office, Communication with Extended European Search Report in application No. 10 794 762.4, dated May 6, 2015 (13 pages).
International Search Report for Intl. App. No. PCT/US15/62637, dated Feb. 1, 2016, 14 pages.
Office Action in U.S. Appl. No. 14/952,348 dated Jan. 20, 2017.
Mclaughlin, et al., "Nitrocinnamoyl and Chlorocinnamoyl Derivatives of Dihydrocodeinone: In Vivo and In Vitro Characterization of µ-Selective Agonist and Antagonist Activity," The Journal of Pharmacology and Experimental Therapeutics, vol. 289, No. 1, 304-311, 1999.
Nieland et al., "Structural Determinants of Opioid Activity in Derivatives of 14-Aminomorphinones: Effect of Substitution in the Aromatic Ring of Cinnamoylaminomorphinones and Codeinones," J. of Medicinal Chemistry, vol. 49, No. 17, 5333-5338, 2006.
Rennison et al., "Cinnamoyl Derivatives of 7α-Aminomethyl-6, 14-endo-ethanotetrahydrothebaine and 7α-Aminomethyl-6, 14-endo-ethanotetrahydrooripavine and Related Opioid Ligands," J. Med. Chem, vol. 50, 5176-5182, 2007.
Notice of Allowance in U.S. Appl. No. 14/816,915 dated Sep. 21, 2017.
Notice of Allowance in U.S. Appl. No. 14/952,348 dated Aug. 25, 2017.
Office Action in U.S. Appl. No. 15/376,211 dated Feb. 8, 2018.
Office Action in Korean Patent Application No. 10-2017-7031555 dated Dec. 11, 2017.
Republic of Costa Rica Industrial Property Registry, "Examiners Report," issued in connection with application No. 2011-0688, dated Oct. 25, 2017.
Republic of Costa Rica, Examination Report, Patent Application No. 2011-688, dated Mar. 22, 2018.
European Patent Office, Communication with Extended European Search Report in application No. 15863639.9, dated Mar. 23, 2018.
IP Australia, "Examination Report No. 1 for standard application," in connection with Application No. 2015353502, dated Mar. 26, 2018.
Intellectual Property Office of Singapore, "Written Opinion," in connection with Application No. 11201704178U, dated Mar. 7, 2018.

(56) References Cited

OTHER PUBLICATIONS

Columbian Patent Office, "Office Action" issued in connection with Columbian Patent Application No. NC2017/0005201, dated Aug. 23, 2018, 10 pgs.

* cited by examiner 4-aminosalicylic acid 3-hydroxyanthranilic acid 3-methoxyanthranilic acid

Salicylates

Aspirin

Diflusinal

Salicylate

Propionates

Ibuprofen

Dexibuprofen

Naproxen

Fenoprofen

Ketoprofen

Dexketoprofen

Flurbiprofen

Oxaprozin

Loxoprofen

Acetates

Indomethacin

Tolmetin

Sulindac

Etodolac

Ketorolac

Diclofenac

Oxicams

Piroxicam

Meloxicam

Tenoxicam

Lornoxicam

Isoxicam

Fenamates

Mefenamic acid

Meclofenamic acid

Flufenamic acid

Tolfenamic acid

Selective COX-2 Inhibitors

Celecoxib

Valdecoxib

Lumiracoxib

Relative Oral PK Curves

Relative Oral PK Curves

BENZOIC ACID, BENZOIC ACID DERIVATIVES AND HETEROARYL CARBOXYLIC ACID CONJUGATES OF OXYCODONE, PRODRUGS, METHODS OF MAKING AND USE THEREOF

RELATED APPLICATIONS

This application is a continuation of U.S. patent application Ser. No. 14/952,348, which was filed on Nov. 25, 2015, which claims the priority of U.S. provisional application Ser. No. 62/084,246, filed Nov. 25, 2014 and U.S. provisional application Ser. No. 62/084,216, filed Nov. 25, 2014, which are incorporated by reference in its entirety.

FEDERALLY SPONSORED RESEARCH OR DEVELOPMENT

[Not Applicable]

BACKGROUND OF THE INVENTION

Opioids are highly effective as analgesics and are commonly prescribed for the treatment of acute and chronic pain. They are also commonly used as antitussives. Opioids, however, also produce euphoria and can be highly addictive. As a result, they are often abused with far reaching social and health related consequences.

Because of the inherent potential for abuse, it is desirable that any pharmaceutical composition containing an opioid agonist be made as abuse-resistant or abuse-deterrent as practical. Illicit users often will attempt, for example, to circumvent the extended release properties of conventional opioid dosage forms/products by injecting or otherwise misusing or tampering with such dosage forms/products in order to achieve an immediate release of the opioid agonist.

Despite their addictive properties and the potential for abuse, morphine-like drugs, particularly, codeine, hydrocodone, and oxycodone have been routinely prescribed as treatment for moderate to severe acute and chronic pain in recent decades. This is, in part, because there are currently no alternative therapies that treat severe pain and do not produce a psychotropic effect other than, for example, the less potent non-steroidal anti-inflammatory drugs (NSAIDS) or central analgesics such as acetaminophen that are typically inadequate to treat severe pain. As a result, there is a need to decrease the abuse potential. Thus far, conventional approaches taken, unfortunately, have not solved the abuse deterrent challenge.

Oxycodone is a semi-synthetic opioid synthesized from poppy-derived thebaine. It is a narcotic analgesic generally indicated for use in managing moderate to moderately severe acute or chronic pain. However, patients taking opioid analgesics such as oxycodone for pain relief can become unintentionally addicted, for example, physically. As tolerance to the opioid develops, more drug is needed to alleviate the pain and generate the sense of well being initially achieved with the prescribed dose. This leads to dose escalation, which if left unchecked can lead rapidly to addiction. In some cases, patients have become very addicted in as little as approximately thirty days. Thus, there is an ongoing need and desire within the medical pain management community for an abuse-resistant or abuse-deterrent opioid product, such as an abuse-resistant or abuse-deterrent oxycodone dosage form and/or product that continues to offer pain relief for moderate to moderately severe pain.

BRIEF SUMMARY OF THE INVENTION

The presently claimed technology utilizes, at least, covalent conjugation of the opioid oxycodone with certain aryl carboxylic acids to decrease its potential for causing overdose or abuse by requiring the active oxycodone to be released through enzymatic or metabolic breakdown of the conjugate in vivo. Aryl carboxylic acids include carboxylic acids that contain an aromatic ring structure. The present technology also provides one or more methods of delivering oxycodone as conjugates that release the oxycodone following oral administration while being resistant to abuse by circuitous routes such as intravenous ("shooting") injection and intranasal administration ("snorting").

The presently described technology, in at least one aspect, provides a slow/sustained/controlled/extended release composition of conjugated oxycodone that allows slow/sustained/controlled/extended delivery of the oxycodone, and/or any active metabolites, into the blood system of a human or animal within a therapeutic window upon, for example, oral administration. At least some compositions/formulations of the currently claimed and described technology can lessen addiction/abuse potential and/or other common side effects associated with oxycodone and similar opioid compounds.

The presently described and claimed technology encompasses one or more compositions having oxycodone covalently attached to at least one aryl carboxylic acid, a derivative thereof, a salt thereof, or a combination thereof. The at least one aryl carboxylic acid is covalently attached to either the C-6 enol tautomer of oxycodone, the C-14 hydroxyl group of oxycodone, or an independently selected aryl carboxylic acid that is attached to both the C-6 enol tautomer and the C-14 hydroxyl groups of oxycodone.

In some embodiments, the aryl carboxylic acid is a benzoate having the following structure:

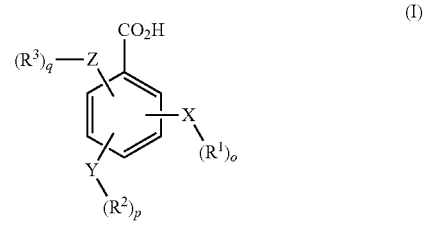

(I)

wherein X, Y and Z are independently selected from the group consisting essentially of H, O, S, NH and $—(CH_2)_x—$; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10, such as 1, 2, 3, 4, 5, 6, 7, 8, 9, and 10.

In another aspect of the present disclosure, the aryl carboxylic acid can be an aminobenzoate, an analog of anthranilic acid, fenamate, hydroxybenzoate, aminohydroxybenzoate, salicylic acid analog, or derivative thereof.

In other aspects of the present technology, the aryl carboxylic acid is, for example, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflusinal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid, or derivatives thereof.

In still another aspect of the present technology, the aryl carboxylic acid can be an aminohydroxybenzoate selected from the group consisting essentially of 4-aminosalicylic acid, 3-hydroxyanthranilic acid, 3-methoxyanthranilic acid, or derivatives thereof.

In another aspect of the present technology, the aryl carboxylic acid is an aminobenzoate can be selected from the group containing, for example, anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid, or derivatives thereof.

In a still further aspect of the present technology, the aryl carboxylic acid is a hydroxybenzoate. For example, the aryl carboxylic acid can be salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflusinal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid, or derivatives thereof.

In a yet a further aspect of the present technology, the aryl carboxylic acid can be a heteroaryl carboxylic acid having one of the following structures:

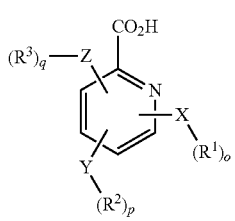

(II)

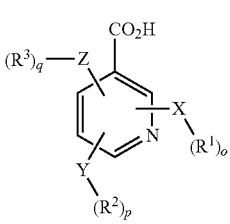

(III)

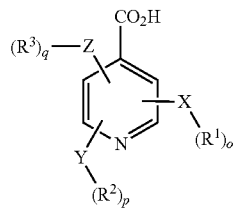

(IV)

wherein X, Y and Z can be independently any combination of H, O, S, NH or $-(CH_2)_x-$. $R^1$, $R^2$ and $R^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl; o, p, q can be independently either 0 or 1; and x is an integer between 1 and 10, such as 1, 2, 3, 4, 5, 6, 7, 8, 9, or 10.

In some aspects of the presently described and claimed technology, the heteroaryl carboxylic acid can be, for example, nicotinic acid (niacin), isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, 7,8-dihydro-7,8-dihydroxykynurenic acid, or derivatives thereof.

In additional aspects of the present disclosure, the aryl carboxylic can be a derivative of phenylacetate having the following general structure:

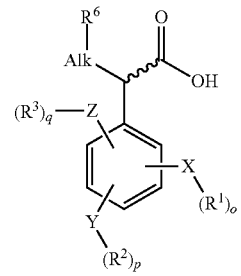

wherein X, Y and Z can be independently any combination of H, O, S, NH or $-(CH_2)_x-$. $R^1$, $R^2$ and $R^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl; o, p, q can be independently either 0 or 1; Alk is an alkyl chain $-(CH_2)_n-$ with n being either 0 or 1; and $R^6$ can be H, OH or carbonyl.

In some aspects of the presently described and claimed technology, the aryl carboxylic can be 2-methyl-2-phenylacetic acid, at least one Non-Steroidal Anti-Inflammatory Drug, a profen, a tyrosine metabolite, or derivatives thereof. Additionally, in further aspects of the present technology, the aryl carboxylic acid can be phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, naproxen, or derivatives thereof.

In yet other aspects of the present technology, aryl carboxylic acid can be an analog of cinnamic acid or phenylpropionic acid having one of the following structures:

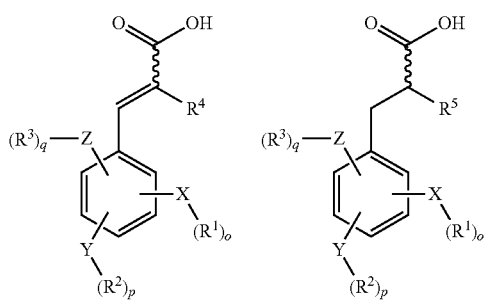

wherein X, Y and Z can be independently any combination of H, O, S, NH or —$(CH_2)_x$—; $R^1$, $R^2$ and $R^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl; o, p, q can be independently either 0 or 1; $R^4$ is H or OH; and $R^5$ is H, and OH or carbonyl; x is an integer between 1 and 10.

In this particular aspect of the presently described and claimed technology, the aryl carboxylic acid can be cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, 2-hydroxy-3-phenylpropenoic acid, or derivatives thereof.

In still further aspects of the present technology, the aryl carboxylic acid can also be a phenylpropionic acid or a substituted derivative thereof. In this aspect of the present technology, the aryl carboxylic acid can be, for example, phenylpropionic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, phenylpyruvic acid, or derivatives thereof.

In another aspect of the present technology, the aryl carboxylic acid can be a phenylacetate or a substituted derivative thereof. In this aspect of the present technology, the aryl carboxylic acid can be, for example, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, naproxen, or derivatives thereof.

The presently described technology further encompasses at least one composition having oxycodone covalently attached to at least one nonsteroidal anti-inflammatory drug (NSAID), a derivative thereof, a salt thereof, or a combination thereof. The at least one NSAID is covalently attached to either the C-6 enol tautomer of oxycodone, the C-14 hydroxyl group of oxycodone, or wherein an independently selected aryl carboxylic acid is attached to both the C-6 enol tautomer and the C-14 hydroxyl group of oxycodone. The NSAID of this and other aspects of the present disclosure can be, for example, a salicylate such as aspirin, diflusinal, or salicylate. The NSAID can also be, for example, a proprionate such as ibuprofen, dexibuprofen, naproxen, fenoprofen, ketoprofen, dexketoprofen, flurbiprofen, oxaprozin, or loxoprofen. The NSAID can also be an acetate such as, for example, indomethacin, tolmetin, sulindac, etodolac, ketorolac, or diclofenac. The NSAID can also be an oxicam such as, for example, piroxicam, meloxicam, tenoxicam, lornoxicam, or isoxicam. The NSAID can also be a fenamate such as, for example, mefenamic acid, meclofenamic acid, flufenamic acid, or tolfenamic acid. The NSAID can also be a selective COX-2 inhibitor such as, for example, celecoxib, valdecoxib, or lumiracoxib.

In yet another aspect, the present technology provides one or more conjugates of oxycodone for use to treat pain, preferably moderate to severe pain, or for use to reduce or prevent oral, intranasal or intravenous drug abuse. In some aspects, the conjugates provide oral, intranasal or parenteral drug abuse resistance or deterrence.

In a further aspect, the present technology provides at least one conjugate of oxycodone that exhibits a slower rate of release over time and a greater or equal AUC when compared to an equivalent molar amount of unconjugated oxycodone over the same time period. In other aspects, the conjugate of oxycodone exhibits less variability in the oral PK profile when compared to unconjugated oxycodone.

In yet another aspect, at least one conjugate has reduced side effects when compared with unconjugated oxycodone or prevents drug tampering by either physical or chemical manipulation. The reduced side effects can include reduced opioid induced constipation.

In yet still further aspect, at least one conjugate of the presently described and claimed technology is provided in an amount sufficient to provide a therapeutically equivalent AUC when compared to an equivalent molar amount of unconjugated oxycodone. In additional aspects, at least one conjugate of the present technology is provided in an amount sufficient to provide a therapeutically equivalent AUC when compared to an equivalent molar amount of unconjugated oxycodone, but does not provide a $C_{max}$ spike, or, alternatively, has a lower $C_{max}$ than a therapeutically equivalent amount of unconjugated oxycodone. In another aspect, at least one conjugate is provided in an amount sufficient to provide a therapeutically equivalent AUC when compared to an equivalent molar amount of unconjugated oxycodone, but does not provide an equivalent $C_{max}$ spike. In some additional aspects, at least one conjugate of the present technology provides an equivalent $C_{max}$ spike when compared to unconjugated oxycodone.

In an additional aspect, the present technology provides at least one method for treating a patient (human or animal) having a disease, disorder or condition requiring or mediated by the binding of an opioid to the opioid receptors of the patient, comprising orally administering to the patient a pharmaceutically or therapeutically effective amount of at least one conjugate of oxycodone disclosed and/or claimed herein.

In a still further aspect, the present technology provides at least one method for treating a patient (human or animal) having a disease, disorder or condition (such as pain) which can be treated by the binding of at least one opioid to the opioid receptors of the patient, the method comprising orally administering to the patient a therapeutically or pharmaceutically effective amount of at least one conjugate of oxycodone, a salt thereof, a derivative thereof or a combination thereof.

In another aspect, the present technology provides a composition that is used to treat narcotic or opioid abuse; to prevent narcotic or opioid withdrawal; to treat moderate to severe pain; to reduce or prevent oral, intranasal or intravenous drug abuse; or to provide oral, intranasal or parenteral drug abuse resistance.

In an additional aspect, the present technology provides at least one method for treating a patient (human or animal) having a disease, disorder or condition (such as addiction) which can be treated by inhibiting binding of at least one opioid to the opioid receptors of the patient, comprising the step of orally administering to the patient a therapeutically or pharmaceutically effective amount of at least one conjugate of oxycodone disclosed and/or claimed herein.

In a yet further aspect, the present technology provides at least one pharmaceutical kit including a specified amount of individual doses in a package containing a therapeutically or pharmaceutically effective amount of at least one conjugate of oxycodone described and/or claimed herein. In some aspects, the kits of the presently described technology can further include one or more instructions regarding use of the kit in a method or manner for treating or preventing drug withdrawal symptoms or pain in a human or animal patient.

DETAILED DESCRIPTION OF THE INVENTION

Figure 1:
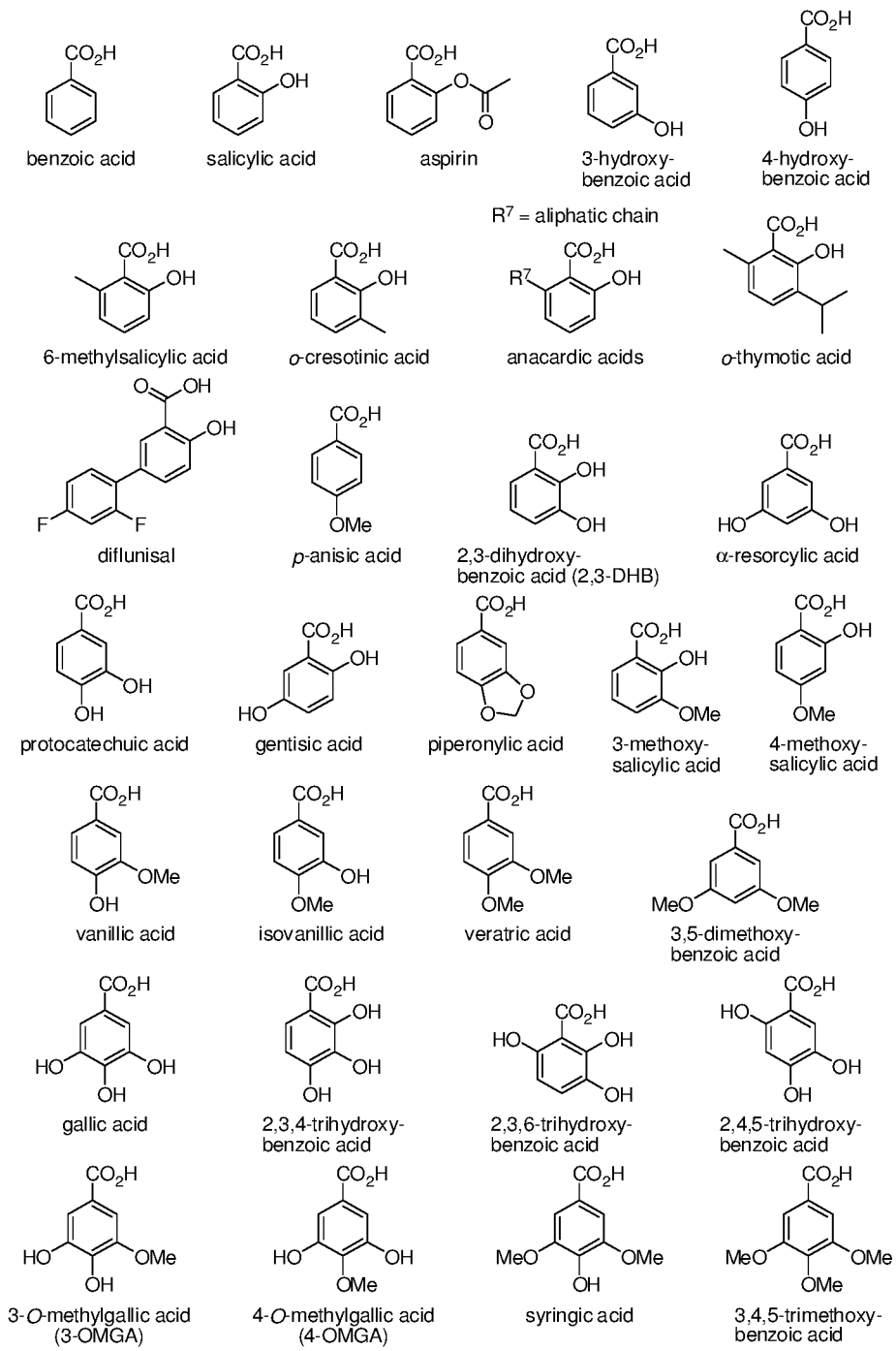
FIG. 1 provides chemical structures of hydroxybenzoic acids and benzoic acid derivatives for use in the making of the conjugates of the present technology.

The present technology provides one or more compositions comprising aryl carboxylic acids chemically conjugated to oxycodone (4,5-α-epoxy-14-hydroxy-17-methylmorphinan-6-one) to form novel conjugates and/or prodrugs and/or compositions of oxycodone. In some embodiments, the chemical bond between these two moieties can be established by reacting the carboxylic acid function of an aryl carboxylic acid with one of the following functional groups of oxycodone: C-6 enol tautomer of oxycodone; C-14 hydroxyl of oxycodone; or both C-14 hydroxyl and C-6 enol tautomer oxycodone.

The use of "oxycodone" is meant to include, for example, a semisynthetic narcotic analgesic and antitussive prepared from codeine with multiple actions qualitatively similar to those of codeine. It is commonly used for the relief of moderate to moderately severe pain. Trade names include, for example, Tylox®, Percodan®, Roxicodone®, Percocet® and OxyContin®. Salt forms of oxycodone, such as oxycodone hydrochloride and oxycodone polistirex, are encompassed by and envisaged within the practice and scope of the presently described and claimed technology.

Aryl carboxylic acids may be grouped into various categories and subcategories. The carboxyl group of the present technology can be attached directly to the aromatic ring or be separated by an alkyl or alkenyl chain. The chain length of the alkyl or alkenyl group of the present technology does not generally exceed two unbranched carbons, but is not limited in the numbers of atoms on potential side-chains or additional functional groups. The present technology includes both carbon only aryl and aryl groups with heteroatoms (heteroaryl). The aryl or heteroaryl group of the present technology, which can be connected directly or through an alkyl or alkenyl chain to the carboxyl function, may be a 6-membered ring and can contain no or one heteroatom. It should be appreciated by those skilled in the relevant art that additional substituted or unsubstituted aromatic or aliphatic rings may be fused to this 6-membered aryl or heteroaryl moiety. The aryl carboxylic acids of the present technology preferably have only one free carboxylic acid group and the total number of phenyl substituents on the 6-membered ring should be four or less.

The aryl carboxylic acids of the presently described and claimed technology may be grouped, without limitation, into one of three main categories of compounds: (1) compounds wherein the carboxylic acid group is directly attached to the aryl moiety; (2) compounds wherein the carboxylic acid group is separated by one carbon from the aryl moiety; and (3) compounds wherein the carboxylic acid group is separated by two carbons from the aryl moiety.

Some embodiments of the present technology provide carboxylic acids conjugated to oxycodone, where the carboxylic acid group is directly attached to the aryl moiety. Carboxylic acids directly attached to the aryl moiety include, for example, benzoates and heteroaryl carboxylic acids.

Some embodiments of the present technology provide at least one conjugate of oxycodone and at least one benzoic acid or benzoic acid derivative, a salt thereof, or a combination thereof. Benzoates are common in nature and include, for example, but are not limited to, aminobenzoates (e.g., anthranilic acid analogs such as fenamates), aminohydroxybenzoates and hydroxybenzoates (e.g., salicylic acid analogs).

The general structure of benzoates of the present technology is:

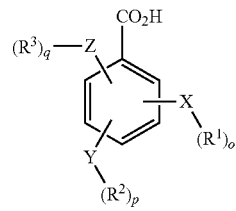

wherein X, Y and Z can be independently any combination of H, O, S, NH or —(CH$_2$)$_x$—; R$^1$, R$^2$ and R$^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl; o, p, q can be independently either 0 or 1; and x is an integer between 1 and 10, such as 1, 2, 3, 4, 5, 6, 7, 8, 9, 10.

In yet additional embodiments, the present technology provides at least one prodrug or composition comprising at least one conjugate of oxycodone and at least one heteroaryl carboxylic acid, a derivative thereof, or a combination thereof. The heteroaryl carboxylic acid can be selected from formula II, formula III or formula IV where formula II, formula III and formula IV are:

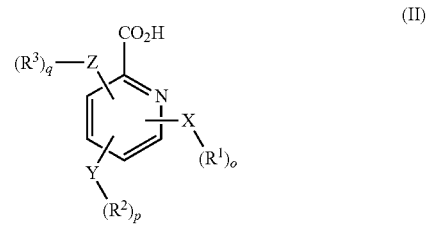

(II)

-continued

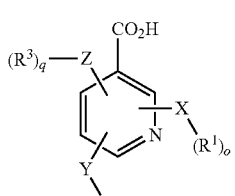

(III)

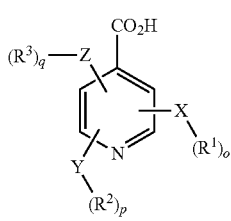

(IV)

wherein X, Y and Z can be independently any combination of H, O, S, NH or —(CH$_2$)$_x$—. R$^1$, R$^2$ and R$^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl. O, p, q can be independently either 0 or 1. X is an integer between 1 and 10, such as 1, 2, 3, 4, 5, 6, 7, 8, 9, 10.

Aryl carboxylic acids with one carbon atom between aromatic ring and carboxyl group of the present technology in some embodiments have the following general structure:

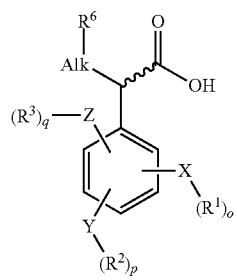

wherein X, Y and Z can be independently any combination of H, O, S, NH or —(CH$_2$)$_x$—. R$^1$, R$^2$ and R$^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl. o, p, q can be independently either 0 or 1. Alk is an alkyl chain —(CH$_2$)$_n$— with n being either 0 or 1. R$^6$ can be H, OH or carbonyl.

Aryl carboxylic acids with the carboxyl group separated by two carbon atoms from the aryl moiety of the present technology have the following general formula:

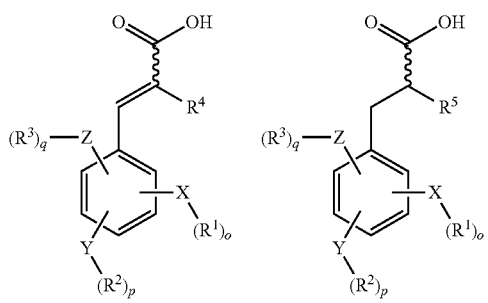

wherein X, Y and Z can be independently any combination of H, O, S, NH or —(CH$_2$)$_x$—. R$^1$, R$^2$ and R$^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl. o, p, q can be independently either 0 or 1. R$^4$ is H or OH; and R$^5$ is H, OH or carbonyl.

Suitable hydroxybenzoic acids (hydroxybenzoates) can be found in FIG. 1 and include, but are not limited to, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflusinal, o,m, p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid, or derivatives thereof.

Figure 2:
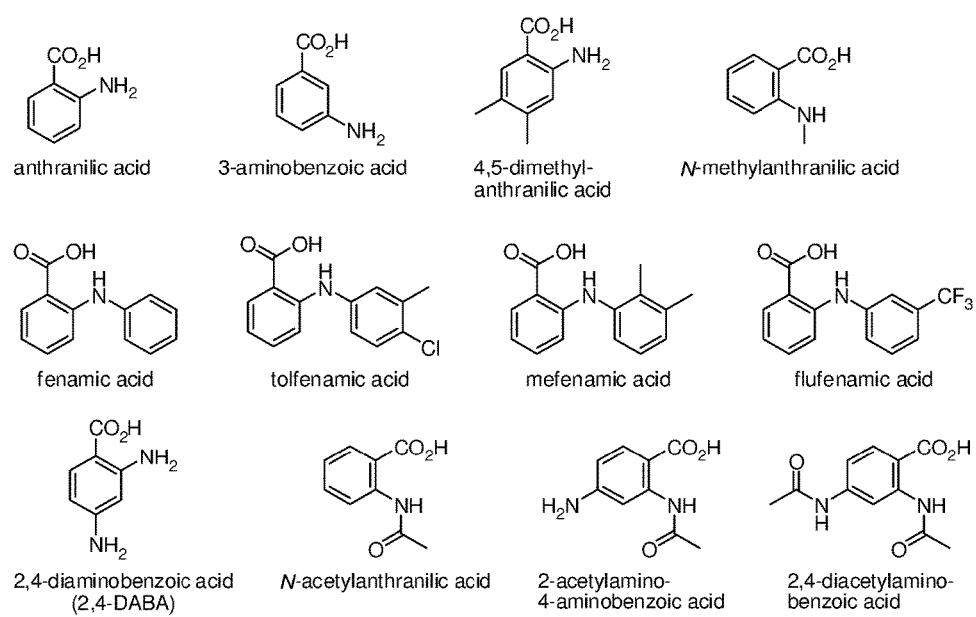
FIG. 2 provides chemical structures of aminobenzoic acids for use in the making of the conjugates of the present technology.

Suitable aminobenzoic acids (aminobenzoates) are shown in FIG. 2 and include, but are not limited to, anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid, or derivatives thereof.

Figure 3:
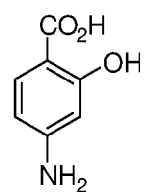
FIG. 3 provides chemical structures of aminohydroxybenzoic acids for use in the making of conjugates of the present technology.
Figure 3:
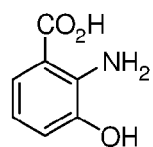
Figure 3:
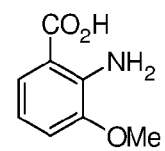

Examples of suitable aminohydroxybenzoic acids that can be used in the practice of the present technology are shown in FIG. 3. These include, but are not limited to, 4-aminosalicylic acid, 3-hydroxyanthranilic acid, or 3-methoxyanthranilic acid.

Figure 4:
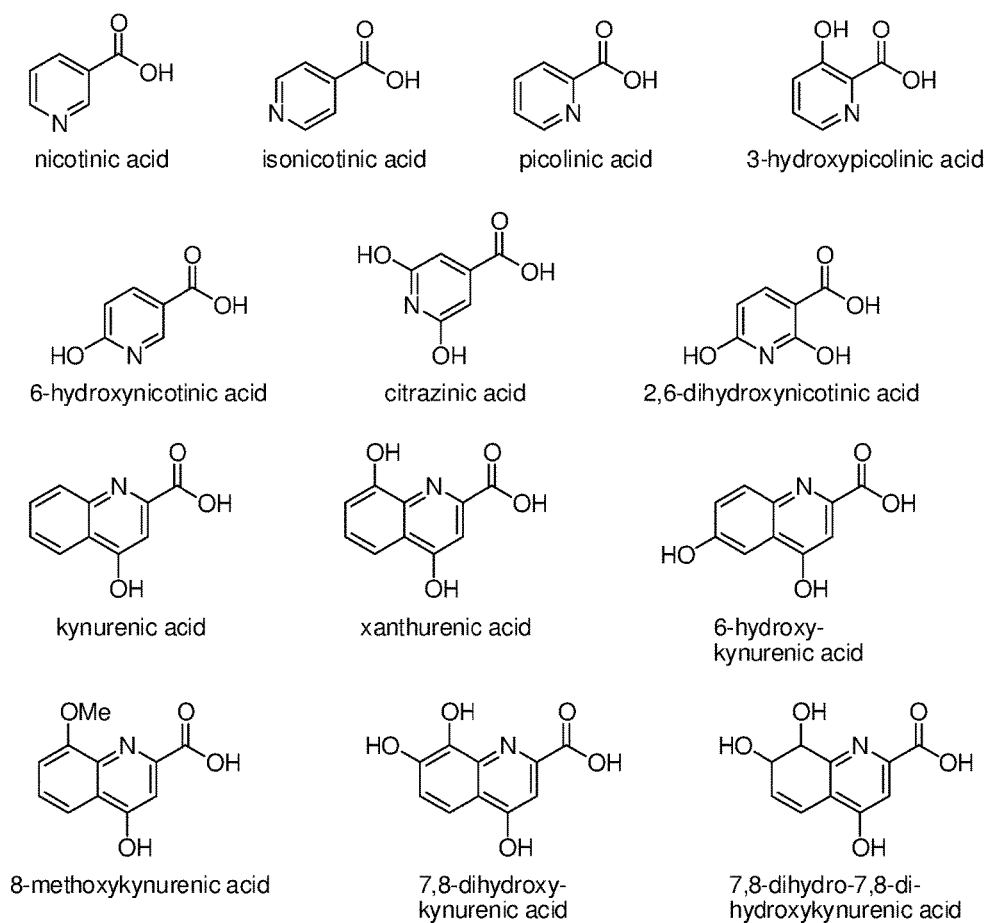
FIG. 4 provides chemical structures of heteroaryl carboxylic acids for use in the making of conjugates of the present technology.

Suitable examples of heteroaryl carboxylic acids include, without limitation, pyridine derivatives, some of which play an important role in the nicotinate and tryptophan metabolism. In these compounds, one carbon of the phenyl ring is replaced by a nitrogen atom. Besides the carboxyl group, this set of compounds can have up to three additional substituents, preferably but not limited to hydroxyl groups Examples of suitable heteroaryl carboxylic acids are shown in FIG. 4 and included, but are not limited to, Nicotinic acid (niacin), isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, 7,8-dihydro-7,8-dihydroxykynurenic acid, or derivatives thereof.

In some embodiments, the compositions of the presently described and claimed technology can include a benzoate conjugate comprising at least one oxycodone conjugated to at least one benzoic acid or benzoic acid derivative, salt thereof or combination thereof.

In further embodiments, the benzoates can include numerous benzoic acid analogs, benzoate derivatives with hydroxyl or amino groups or a combination of both. The hydroxyl and amino functions may be present in their free form or capped with another chemical moiety, preferably but not limited to methyl or acetyl groups. The phenyl ring can have additional substituents, but the total number of substituents can be four or less, three or less, or two or less.

In some embodiments, the carboxy group of the aryl carboxylic acids can be attached directly to the aromatic ring. The present technology includes both carbon-only aryl groups and aryl groups with heteroatoms (heteroaryl). The aryl or heteroaryl group which is connected directly to the carboxyl function can be a 6-membered ring and contains no or one heteroatom. In various embodiments, the additional substituted or unsubstituted aromatic or aliphatic rings can be fused to this 6-membered aryl or heteroaryl moiety. In further embodiments, the aryl carboxylic acids may have only one free carboxylic acid group and the total number of phenyl substituents on the 6-membered ring should be four or less, for example, 4, 3, 2 or 1.

In still further embodiments of the present technology, depending on the individual aryl carboxylic acid that is connected to oxycodone, the conjugate of oxycodone can have a neutral, free acid, free base, or various pharmaceutically acceptable anionic or cationic salt forms or salt mixtures with any ratio between positive and negative components. These salt forms include, but are not limited to: acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminium, lithium, cholinate, lysinium, ammonium, tromethamine, or derivatives thereof.

Some embodiments of the present technology provide aryl carboxylic acids conjugated to oxycodone, where the carboxylic acid group is separated by one carbon from the aryl moiety. Aryl carboxylic acids in this category can include, without limitation, branched phenylpropionic acids (i.e., 2-methyl-2-phenylacetates) or other derivatives of phenylacetate. Examples of these compounds are certain types of NSAIDs (Non-Steroidal Anti-Inflammatory Drugs), such as profens, or tyrosine metabolites.

Figure 5:
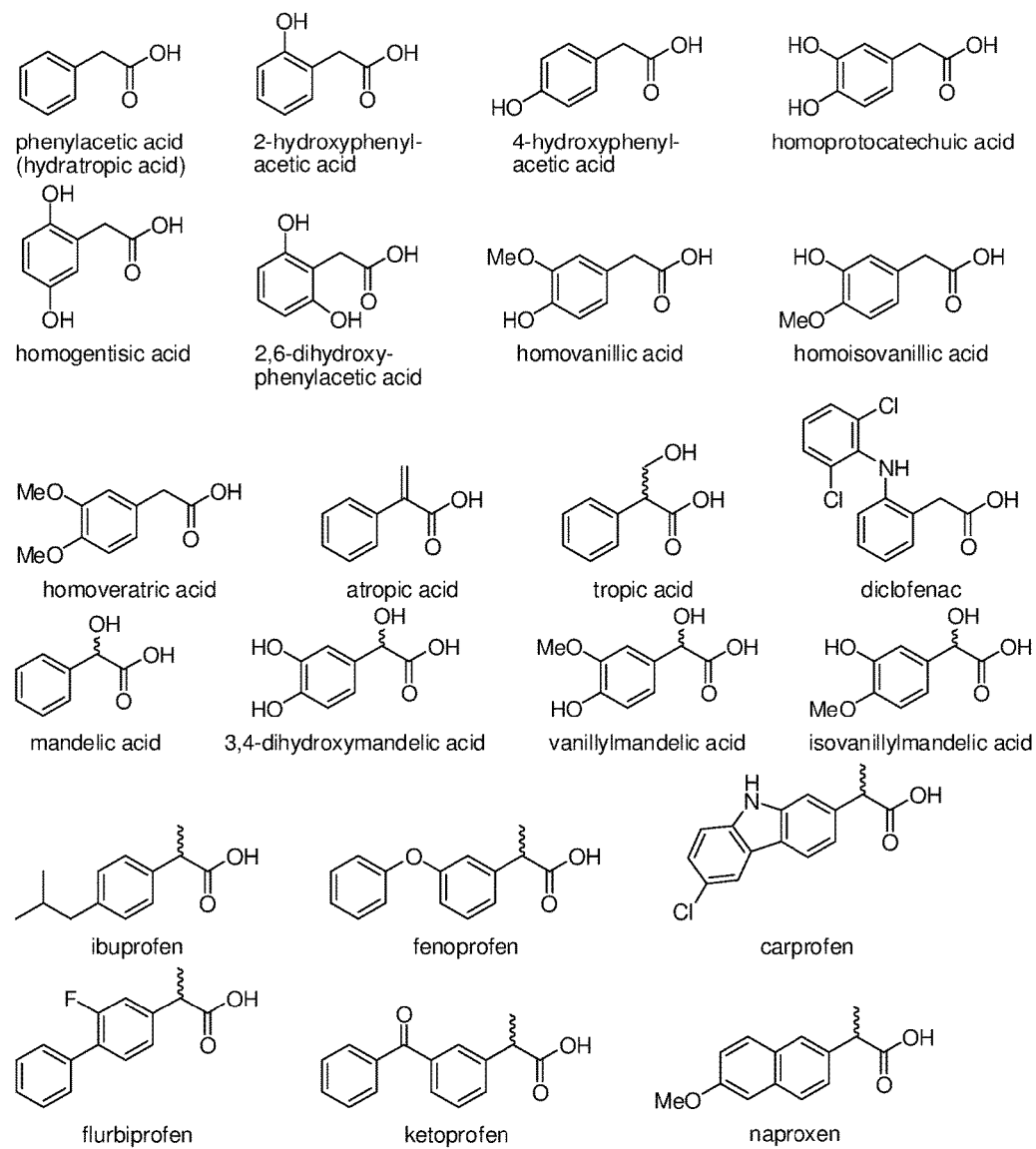
FIG. 5 provides chemical structures of phenylacetates for use in the making of conjugates of the present technology.

Examples of phenylacetates for use in the practice of the present technology are shown in FIG. 5 and include, without limitation, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, or naproxen.

Some embodiments of the present technology provide aryl carboxylic acids conjugated to oxycodone, wherein the carboxylic acid group is separated by two carbons from the aryl moiety. This category of aryl carboxylic acids includes, without limitation, phenylpropionic acids and substituted derivatives thereof and analogs of cinnamic acid. These compounds are abundant in nature in the form of natural products or metabolites (e.g., phenylalanine metabolism).

Phenylpropionic acids have an ethylene group between the carboxyl function and the phenyl ring. Both the alkyl chain and the aryl moiety, can have substituents, such as, for example, hydroxyl groups. Some compounds of this class can be found in the phenylalanine metabolism.

Figure 6:
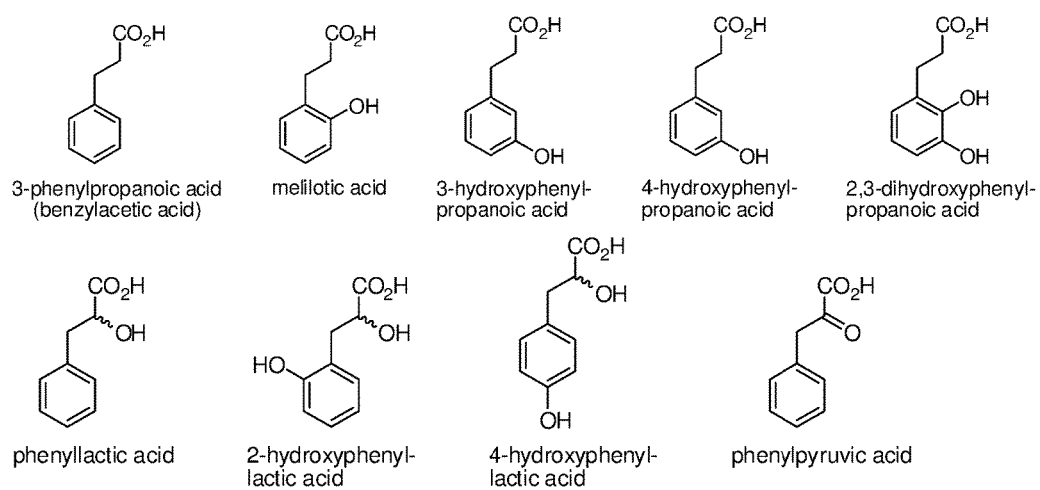
FIG. 6 provides chemical structures of phenylproprionates for use in the making of conjugates of the present technology.

Examples of phenylpropionic acids that can be used in the practice of the present technology are shown in FIG. 6 and include, without limitation, phenylpropionic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, phenylpyruvic acid, or derivatives thereof.

Figure 7:
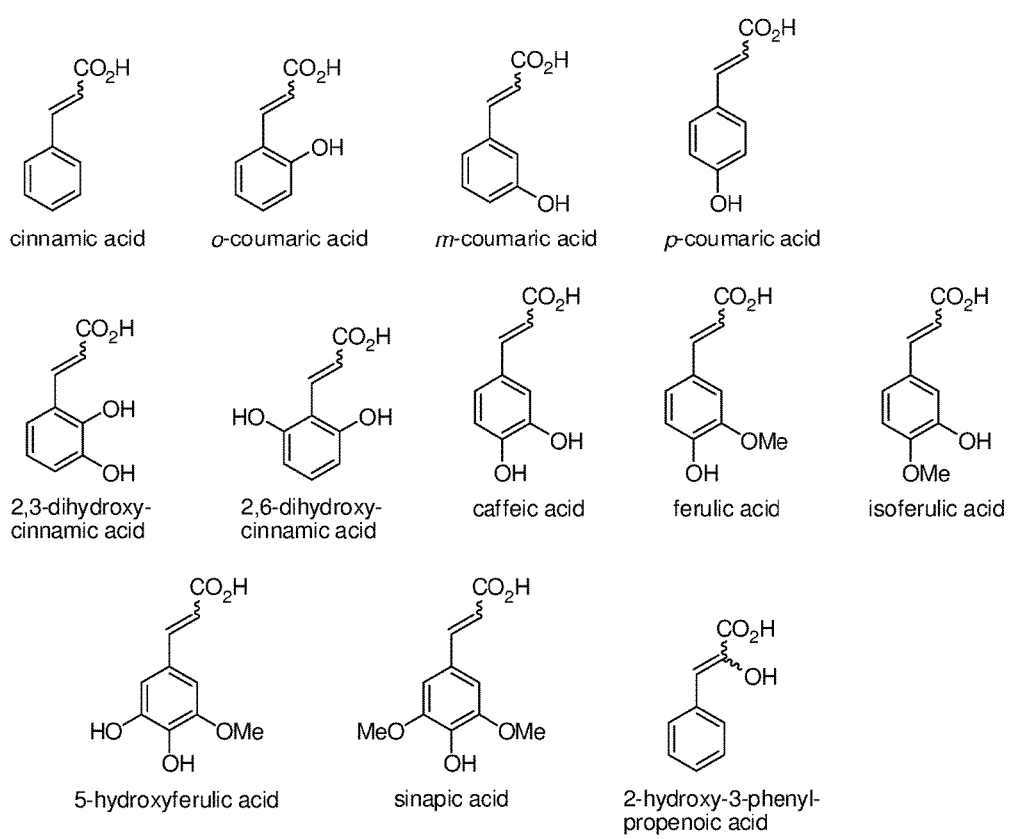
FIG. 7 provides chemical structures of cinnamates for use in the making of conjugates of the present technology.

Cinnamic acids (3-phenylacrylic acids) are unsaturated analogs of phenylpropionic acids. Cinnamates occur in two isomeric forms: cis (Z) and trans (E). The isomers of this invention are not limited to but are preferably in the trans configuration. Similar to phenylpropionic acids, derivatives of cinnamic acid can be substituted on the alkenyl or aryl moiety of the molecule. Preferred substituents are hydroxyl and methoxy groups. Certain cinnamates play a key role in the phenylalanine metabolism Examples of cinnamates that can be used in the practice of the present technology are shown in FIG. 7 and include, without limitation, Cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, 2-hydroxy-3-phenylpropenoic acid, or derivatives thereof.

Figure 8:
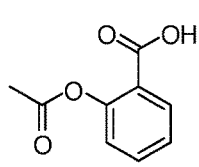
FIG. 8 provides chemical structures of NSAID salicylates for use in the making of conjugates of the present technology.
Figure 8:
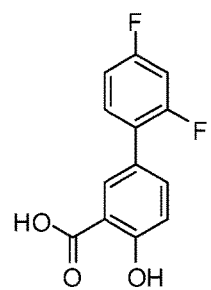
Figure 8:
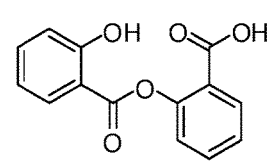
Figure 9:
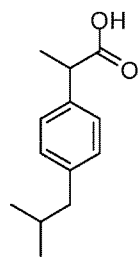
FIG. 9 provides chemical structures of NSAID propionates for use in the making of conjugates of the present technology.
Figure 9:
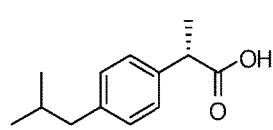
Figure 9:
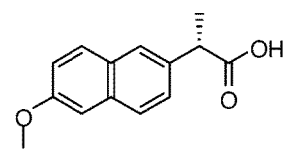
Figure 9:
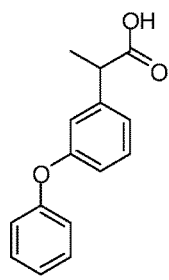
Figure 9:
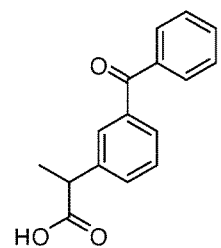
Figure 9:
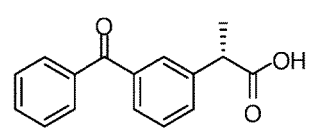
Figure 9:
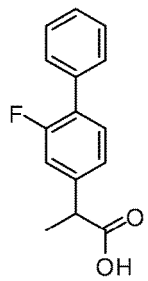
Figure 9:
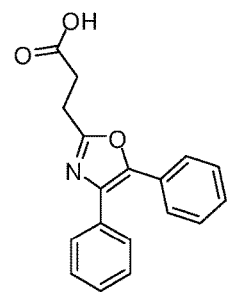
Figure 9:
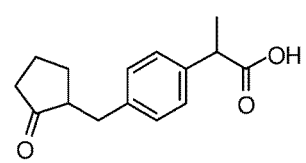
Figure 10:
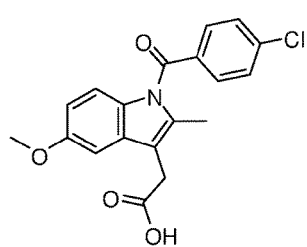
FIG. 10 provides chemical structures of NSAID acetates for use in the making of conjugates of the present technology.
Figure 10:
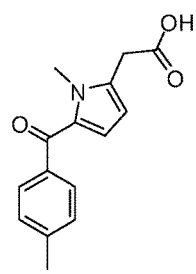
Figure 10:
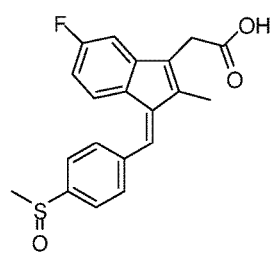
Figure 10:
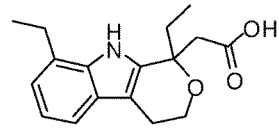
Figure 10:
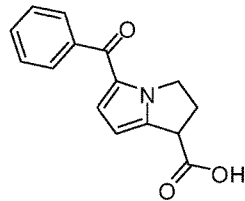
Figure 10:
Figure 11:
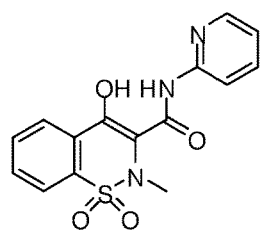
FIG. 11 provides chemical structures of NSAID oxicams for use in the making of conjugates of the present technology.
Figure 11:
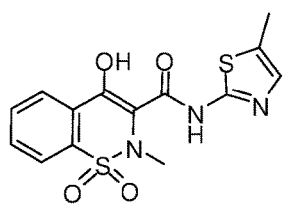
Figure 11:
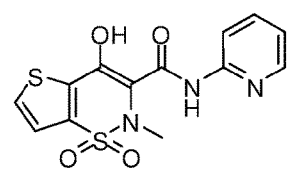
Figure 11:
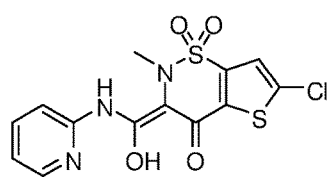
Figure 11:
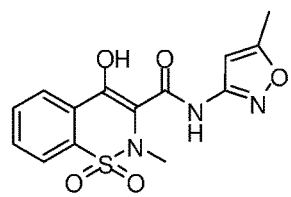
Figure 12:
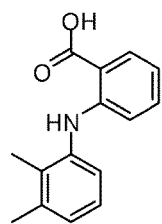
FIG. 12 provides chemical structures of NSAID fenamates for use in the making of conjugates of the present technology.
Figure 12:
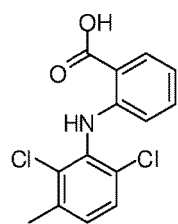
Figure 12:
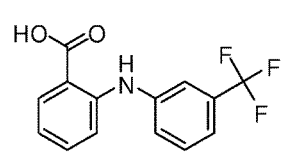
Figure 12:
Figure 13:
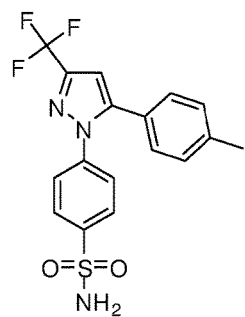
FIG. 13 provides chemical structures of NSAID selective COX-2 inhibitors for use in the making of conjugates of the present technology.
Figure 13:
Figure 13:
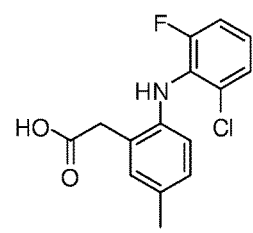

Some embodiments of the present technology provide at least one composition having oxycodone covalently attached to at least one nonsteroidal anti-inflammatory drug (NSAID), a derivative thereof, a salt thereof, or a combination thereof. The at least one NSAID is covalently attached to either the C-6 enol tautomer of oxycodone, the C-14 hydroxyl group of oxycodone, or wherein an independently selected aryl carboxylic acid is attached to both the C-6 and C-14 hydroxyl group of oxycodone. The NSAID can be, for example, a salicylate such as aspirin, diflusinal, or salicylate (see, e.g., FIG. 8). The NSAID can also be, for example, a proprionate such as ibuprofen, dexibuprofen, naproxen, fenoprofen, ketoprofen, dexketoprofen, flurbiprofen, oxaprozin, loxoprofen, or derivatives thereof (see, e.g., FIG. 9). The NSAID can also be an acetate such as, for example, indomethacin, tolmetin, sulindac, etodolac, ketorolac, diclofenac, or derivatives thereof (see, e.g., FIG. 10). The NSAID can be an oxicam such as, for example, piroxicam, meloxicam, tenoxicam, lornoxicam, isoxicam, or derivatives thereof (see, e.g., FIG. 11). The NSAID can also be a fenamate such as, for example, mefenamic acid, meclofenamic acid, or flufenamic acid, tolfenamic acid, or derivatives thereof (see, e.g., FIG. 12). The NSAID can also be a selective COX-2 inhibitor such as, for example, celecoxib, valdecoxib, lumiracoxib, or derivatives thereof (see, e.g., FIG. 13).

Some embodiments of the present technology provide at least one conjugate of oxycodone that is broken down in vivo either enzymatically or chemically when administered via the intended route, releasing the active oxycodone and the respective aryl carboxylic acid or metabolites thereof. The aryl carboxylic acids used in the conjugates of the present technology are preferably non-toxic at the given dosing levels and are preferably known drugs, natural products, metabolites, or GRAS (Generally Recognized As Safe) compounds (e.g., preservatives, dyes, flavors, etc.) or nontoxic mimetics thereof, including natural, synthetic, or both.

Compounds, conjugates, products, prodrugs, compositions and methods of the present technology provide, for example, reduced potential for overdose, reduced potential for abuse or addiction and/or improve oxycodone's characteristics with regard to side effect profiles or suboptimal release profiles. Without wishing to be limited to the below theory, it is believed that the presently described and claimed technology provides abuse resistance via intranasal and intravenous routes, because the described and claimed conjugates, compounds, compositions, prodrugs, and/or products are exposed to different enzymes and/or metabolic pathways upon oral administration where the conjugates, compounds, compositions, products and/or prodrugs are exposed to enzymes in the gut and first-pass metabolism as opposed to exposure to enzymes in the circulation or mucosal membranes which limits the ability of the oxycodone from being released from the conjugate. Therefore, abuse resistance and/or abuse deterrence is provided by limiting the "rush" or "high" available from the active oxycodone released by the prodrug, product, composition, compound, and/or conjugate of the present technology and limiting the effectiveness of alternative routes of administration.

The compositions of the present technology preferably have no or a substantially decreased pharmacological activity when administered through injection or intranasal routes of administration. However, they remain orally bioavailable. Again, not wanting to be bound by any particular theory, the bioavailability of the compositions of the present technology can be a result of the hydrolysis of the chemical linkage (i.e., a covalent linkage) following oral administration. In at least one embodiment of the present technology, release of oxycodone is delayed, reduced or prevented when the composition, compound, conjugate, product, or prodrug of the present technology is delivered, for example, by parenteral routes.

For example, in at least one embodiment, the composition of the present technology maintains its effectiveness and abuse resistance and/or deterrence following the crushing of the tablet, capsule or other oral dosage form. In contrast, from non-conjugated (or "unconjugated") formulations of oxycodone, the oxycodone is released immediately following crushing allowing the content of the crushed tablet to be used by injection or snorting, in turn, producing the "rush" effect sought by addicts.

In other embodiments of the present technology, the conjugates of oxycodone can be given orally to an animal or human patient, and, upon administration, release the active oxycodone by being hydrolyzed in the body. Not to be bound by any particular theory, it is believed that since the aryl carboxylic acids are naturally occurring metabolites or mimetics thereof or pharmaceutically active compounds, these conjugates can be easily recognized by physiological systems resulting in hydrolysis and release of oxycodone. The conjugates themselves have either no or limited pharmacological activity as a conjugate and consequently may follow a metabolic pathway that differs from the parent drug.

In some embodiments of the present technology, the choice of a suitable aryl carboxylic acid ("ligands") to conjugate to oxycodone determines the release of oxycodone into the systemic circulation and can be controlled even when the conjugate is administered via routes other than oral. In one embodiment, the modified oxycodone would release oxycodone similar to free or unmodified oxycodone when administered orally. In another embodiment, the conjugated oxycodone releases oxycodone in a controlled, extended or sustained form or manner when administered orally. In further embodiments, this controlled/sustained/extended release can alleviate certain side-effects and improve upon the safety profile, or the abuse profile, or both of the parent drug. These side-effects may include, but are not limited to, anxiety, bruising, constipation, decreased appetite, difficulty breathing, dizziness, drowsiness, dry throat, dry mouth, lethargy, somnolence, pruritus, diarrhea, headache, nausea, stomach cramps, stomach pain, abdominal pain, dyspepsia, gastritis, chills, fever, anorexia, twitching, abnormal dreams, confusion, dysphoria, euphoria, insomnia, nervousness, thought abnormalities, dyspnea, hiccups, rash, hypotension, lymphadenopathy, tinnitus, abnormal vision, dysphagia, eructation, flatulence, gastrointestinal disorder, increased appetite, stomatitis, withdrawal symptom, seizures, edema, peripheral edema, thirst, malaise, chest pain, facial edema, ST depression, dehydration, syncope, migraine, abnormal gait, amnesia, hyperkinesia, hypoesthesia, hypotonia, paresthesia, speech disorder, stupor, tremor, vertigo, taste perversion, depression, agitation, depersonalization, emotional lability, hallucination, dysuria, hematuria, polyuria, urinary retention, impotence, cough increased, voice alteration, dry skin, exfoliative dermatitis, abuse, addiction, amenorrhea, cholestasis, death, dental caries, increased hepatic enzymes, hyperalgesia, hypogonadism, hyponatremia, ileus, muscular hypertonia, overdose, palpitations, syndrome of inappropriate antidiuretic hormone secretion, urticarial, anaphylaxis, or vomiting. In yet another embodiment, the conjugated oxycodone would selectively allow oxycodone to be metabolized to oxymorphone. In some embodiments, these conjugates can be used for pain relief, such as moderate to severe pain relief yet in an abuse resistance or deterrent manner and with the further potential of reduced or prevented side effects of the parent drug or the metabolite thereof.

Oxycodone and other opioids are also highly addictive and prone to abuse. Recreational drug abuse of opioids is a common problem and usually begins with oral doses taken with the purpose of achieving euphoria ("rush" or "high"). Over time the drug abuser often increases the oral dosages to attain more powerful "highs" or to compensate for heightened opioid tolerance. This behavior can escalate and result in exploring other routes of administration such as intranasal ("snorting") and intravenous ("shooting").

In some embodiments of the present technology, the oxycodone that is conjugated with a suitable aryl carboxylic acid ligand does not result in rapid spikes in plasma concentrations after oral administration that is sought by a potential drug abuser. In other embodiments, oxycodone released from these conjugates has a delayed $T_{max}$ and possibly lower $C_{max}$ than the unconjugated oxycodone. Not to be bound by any particular theory, it is believed that the conjugates of the present technology, when taken orally or by other non-oral routes, do not provide the feeling of a "rush" even when taken at higher doses, but still initially provide and/or maintain pain relief.

Additionally, in some embodiments, oxycodone conjugated with appropriate ligands of the present technology is not hydrolyzed efficiently when administered via non-oral routes. As a result, these conjugates do not generate high plasma or blood concentrations of released oxycodone when injected or snorted as compared to free oxycodone administered through these same routes.

In further embodiments, the conjugates of the present technology, since they consist of covalently bound oxycodone, are not able to be physically manipulated to release the oxycodone opioid from the conjugated oxycodone by various methods, for example, by grinding or crushing solid dosage forms. Moreover, the conjugates of the present technology exhibit resistance to chemical hydrolysis under conditions a potential drug abuser may apply to "extract" the active portion of the molecule, for example, by boiling, or acidic or basic solution treatment of the conjugate. Such resistance offers significant advantages over conventional dosage forms and products of oxycodone.

The compositions, compounds, conjugates and prodrugs of the present technology can be oral dosage forms. These dosage forms include, but are not limited to tablet, capsule, caplet, troche, lozenge, powder, suspension, syrup, solution, or oral thin film (OTF) dosage forms. Preferred oral administration forms are capsule, tablet, solutions and OTF dosage forms.

Solid dosage forms can include, but are not limited to, the following types of excipients: anti-adherents, binders, coatings, disintegrants, fillers, flavors, dyes, colors, glidants, lubricants, preservatives, sorbents, sweeteners, derivatives thereof, or combinations thereof.

Oral formulations of the present technology can also be included in a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow, for example.

Soft gel or soft gelatin capsules may be prepared, for example, by dispersing the formulation in an appropriate vehicle (vegetable oils are commonly used) to form a high viscosity mixture. This mixture is then encapsulated with a gelatin-based film using technology and machinery known to those in the soft gel industry. The individual units so formed are then dried to constant weight as a final product for administration to a human or animal patient.

Chewable tablets, for example, may be prepared by mixing the compounds, compositions, conjugates, prodrugs, or formulations of the present technology with excipients designed to form a relatively soft, flavored, tablet dosage form that is intended to be chewed rather than swallowed. Conventional tablet machinery and procedures, for example, direct compression and granulation, i.e., or slugging, before compression, can be utilized. Those individuals involved in pharmaceutical solid dosage form production are versed in the processes and the machinery used, as the chewable dosage form is a very common dosage form in the pharmaceutical industry.

Film coated tablets, for example, may be prepared by coating tablets using techniques such as rotating pan coating methods or air suspension methods to deposit a contiguous film layer on a tablet containing the compounds, conjugates, compositions, prodrugs or formulations of the present technology.

Compressed tablets, for example, may be prepared by mixing the formulation with excipients intended to add binding qualities to disintegration qualities. The mixture is either directly compressed, or granulated and then compressed using methods and machinery known to those in the pharmaceutical compounding industry. The resultant compressed tablet dosage units are then packaged according to market need, for example, in unit dose, rolls, bulk bottles, blister packs, etc.

The present technology also contemplates the use of biologically-acceptable carriers which may be prepared from a wide range of materials. Without being limited to, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, silicon dioxide, and derivatives thereof.

It should be understood that in addition to the ingredients particularly mentioned above, the formulations of the present technology can include other suitable agents such as flavoring agents, preservatives and antioxidants, among others. Such antioxidants are preferably food acceptable and could include, for example, vitamin E, carotene, BHT or other antioxidants or derivatives thereof.

Other compounds, which may be included in the compositions, compounds, conjugates, formulations and/or prodrugs of the present technology, by admixture are, for example, medically inert ingredients, e.g., solid and liquid diluents, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulfates; or other therapeutically acceptable accessory ingredients, such as humectants, preservatives, buffers and antioxidants, which are known additives for such formulations.

For oral administration of various embodiments of the present technology, fine powders or granules containing comminuting, diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable, flavoring, preserving, suspending, thickening or emulsifying agents can also be included.

Liquid dispersions for oral administration may be syrups, emulsions or suspensions. The syrups may contain as carrier, for example, saccharose or saccharose with glycerol and/or mannitol and/or sorbitol. In particular, a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose polyvinyl alcohol, or derivatives or combinations thereof.

Formulations of oxycodone of the present technology can be, for example, combination therapies of oxycodone and one or more other non-narcotic active ingredient depending on intended indication or off-label usage/application. Examples of these active pharmaceuticals include, but are not limited to, acetaminophen, phenylpropanolamine, homatropine, ibuprofen, aspirin, pheniramine, chlorpheniramine, phenylephrine, pseudoephedrine, pyrilamine, guaifenesin, and derivatives and combinations thereof. The conjugated oxycodone of the present technology can be formulated with one or a combination of these or other active substances, among others, or as standalone active ingredient without any other actives.

The conjugates, compounds, compositions, formulations, and/or prodrugs of the present technology may be used in methods of treating a patient (human or animal) having a disease, disorder or condition requiring or mediated by binding or inhibiting binding of an opioid to the opioid receptors of the patient. Treatment comprises the step orally administering to the patient a therapeutically effective amount of at least one conjugate, compound, composition, prodrug, or formulation of oxycodone as described in the present technology. The conjugate can exhibit a slower rate of release over time and AUC when compared to an equivalent molar amount of unconjugated oxycodone. In other embodiments, at least one conjugate, compound, composition, prodrug, or formulation of the present technology can exhibit less variability in the oral PK profile when compared to unconjugated oxycodone.

In other embodiments, at least one oxycodone conjugate, compound, composition, prodrug, or formulation of the present technology is provided in an amount sufficient to provide a therapeutically equivalent AUC (area under the curve) when compared to a molar equivalent amount of unconjugated oxycodone. In further embodiments, the oxycodone conjugate, composition, compound, formulation, or prodrug of the present technology is provided in an amount sufficient to provide a therapeutically equivalent AUC when compared to unconjugated oxycodone but has a lower $C_{max}$ (peak concentration) in plasma or does not provide an equivalent $C_{max}$ in plasma concentrations. In some aspects, the conjugate, composition, compound, formulation, or prodrug of the present technology is provided in an amount sufficient to provide a therapeutically equivalent $C_{max}$ when compared to unconjugated oxycodone.

Suitable diseases, disorders or conditions that can be treated by the prodrugs or compositions of the present technology are narcotic addiction or drug addiction and/or acute or chronic pain, among others.

The prodrugs, compositions, compounds, conjugates, or formulations of the present technology can be, without limitation, prepared in oral dosage forms. These dosage forms include but are not limited to tablet, capsule, caplet, troche, lozenge, powder, suspension, syrup, solution or oral thin film (OTF). Example oral administration forms are capsule, tablet, solutions and OTF. Solid dosage forms can include the following types of excipients: antiadherents, binders, coatings, disintegrants, fillers, flavors and colors, glidants, lubricants, preservatives, sorbents and sweeteners. Current approved formulations of oxycodone are tablets, capsules, modified release capsules, extended release tablets, controlled release capsules, suppository, powder for injection, oral liquid, cough syrup, and injections.

Dosages for the conjugates of the present technology depend on their molecular weight and the respective weight-percentage of oxycodone as part of the whole conjugate, and therefore can be higher than the dosages of free oxycodone. Oral dosage strengths based on oxycodone hydrochloride range from about 2.5 mg to about 30 mg for immediate release formulations and from about 10 mg to about 80 mg for extended release formulations. Doses should be titrated to appropriate analgesic effects while minimizing adverse effects. Some example doses include, without limitation, 2.5, 4.8355, 5, 7.5, 10, 15, 20, 30, 40, 60, 80 mg. Dosages for the conjugates of the present technology can be higher depending on their molecular weight and the respective weight-percentage of oxycodone as part of the whole conjugate. Dose conversion from oxycodone hydrochloride to oxycodone prodrug can be performed using the following formula:

$$\text{dose(OC prodrug)} = f_{BA} \times \text{dose(OC·HCl)} \times \frac{\text{MW(OC prodrug)}}{351.83 \frac{g}{mol}}$$

OC=oxycodone
HCl=hydrochloride
MW=molecular weight
$f_{BA}$=correction factor accounting for differences in bioavailability between unmodified oxycodone and prodrugs or conjugates of this invention.

Suitable exemplar dosages of the conjugated oxycodone of the present technology include, but are not limited to, formulations including from about 0.5 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher, and include any additional increments thereof, for example, 0.1, 0.2, 0.25, 0.3, 0.4, 0.5, 0.6, 0.7, 0.75, 0.8, 0.9 or 1.0 mg and multiplied factors thereof, (e.g., ×2, ×2.5, ×5, ×10, ×100, etc.). The present technology also includes dosage formulations including currently approved formulations of oxycodone, where the dosage can be calculated using the above-noted formula determined by the amount of oxycodone hydrochloride. The present technology provides for dosage forms formulated as a single therapy or as a combination therapy with other active pharmaceutical ingredients.

The conjugates of oxycodone with derivatives of NSAID of the present technology have a number of advantages including, but not limited to, a reduced patient variability of plasma concentrations of oxycodone when compared to free oxycodone, reduced drug abuse potential, reduced risk of chemical or physical manipulation resulting in full dosage of oxycodone released, improved dosage forms through covalent linkage to aryl carboxylic acids or derivatives thereof, increased or decreased metabolism of oxycodone and/or decreased side-effects other than drug abuse.

Side effects of opioid analgesics include gastrointestinal dysfunction caused by the opioids binding to the mu ($\mu$) receptors present in the gastrointestinal tract. The side-effects in the stomach can include a reduction in the secretion of hydrochloric acid, decreased gastric motility, thus prolonging gastric emptying time, which can result in, for example, esophageal reflux. Passage of the gastric contents through the duodenum may be delayed by as much as 12 hours, and the absorption of orally administered drugs is retarded. In the small intestines, the opioid analgesics diminish biliary, pancreatic and intestinal secretions and delay digestion of food in the small intestine. Propulsive peristaltic waves in the colon are diminished or abolished after administration of opioids, and tone is increased to the point of spasm. The resulting delay in the passage of bowel contents causes considerable desiccation of the feces, which, in turn retards their advance through the colon. These actions, combined with inattention to the normal sensory stimuli for defecation reflex due to the central actions of the drug, contribute to opioid-induced constipation or "OIC."

Oxycodone is used for the treatment of moderate to severe pain. The prodrugs of the present technology may be administered for the relief of pain or for the treatment of any condition that may require the blocking of opioid receptors. The conjugates of the present technology can provide a decrease in side effects of the opioid analgesic, including reduced or inhibited constipatory effects.

The present technology also provides a method of synthesis for the preparation of the conjugated oxycodone of the present technology. In one embodiment, the synthesis of the present technology includes the steps of: protection of the ligand, if necessary; activation of the ligand carboxylic acid group, if not already in activated form; addition of the activated ligand to oxycodone or vice versa in the presence of base; and removal of ligand protecting groups, if applicable.

If the aryl carboxylic acid contains any additional reactive functional groups that may interfere with the coupling to oxycodone, it may be necessary to first attach one or more protecting groups. Any suitable protecting group may be used depending on the type of functional group and reaction conditions. Some protecting group examples are: acetyl (Ac), β-methoxyethoxymethyl ether (MEM), methoxymethyl ether (MOM), p-methoxybenzyl ether (PMB), trimethylsilyl (TMS), tert.-butyldimethylsilyl (TBDPS), triisopropylsilyl (TIPS), carbobenzyloxy (Cbz), p-methoxybenzyl carbonyl (Moz), tert.-butyloxycarbonyl (Boc), 9-fluorenylmethyloxycarbonyl (Fmoc), benzyl (Bn), p-methoxybenzyl (MPM), tosyl (Ts). Temporary formation of acetals or ketals from carbonyl functions may also be appropriate.

The carboxylic acid group of the ligands should be activated in order to react with oxycodone and to generate appreciable amounts of conjugate. This activation can be accomplished in numerous ways by a variety of coupling agents known to one skilled in the art. Examples of such coupling agents are: N,N-dicyclohexylcarbodiimide (DCC), N-(3-dimethylaminopropyl)-N'-ethylcarbodiimide (EDCI), N,N'-diisopropylcarbodiimide (DIC), 1,1'-carbonyldiimidazole (CDI) or other carbodiimides; (benzotriazol-1-yloxy)tris(dimethylamino)phosphonium hexafluorophosphate (BOP), bromotripyrrolidinophosphonium hexafluorophosphate (PyBroP), (benzotriazol-1-yloxy)tripyrrolidinophosphonium hexafluorophosphate (PyBOP) or other phosphonium-based reagents; O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), fluoro-N,N,N',N'-tetramethylformamidinium hexafluorophosphate (TFFH), N,N,N',N'-tetramethyl-O—(N-succinimidyl)uronium tetrafluoroborate (TSTU) or other aminium-based reagents. The aryl carboxylic acid can also be converted to a suitable acyl halide, acyl azide or mixed anhydride.

A base may be required at any step in the synthetic scheme of an aryl carboxylic acid conjugate of oxycodone. Suitable bases include but are not limited to: 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine or any other tertiary amine.

Suitable solvents that can be used for any reaction in the synthetic scheme of an aryl carboxylic acid conjugate of oxycodone include but are not limited to: acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

In some embodiments, the prodrug is hydrophobic and thus poorly water soluble. This results in a gel-like consistency or clumpy suspension when the compound is mixed with water. Not to be bound by any theory, it is believed that these compounds would also congeal or become clumpy when a human subject (or animal subject) tries to inhale them intranasally ("snorting"). This property would not only make an attempt of intranasal abuse an unpleasant experience but would likely also prevent the prodrug from permeating the nose mucosa. As a consequence, these compounds become ineffective for this route of administration.

The present technology also provides for pharmaceutical kits for the treatment or prevention of drug withdrawal symptoms or pain in a patient (human or animal). The patient may be a human or animal patient. Suitable human patients include, for example, pediatric patients, geriatric (elderly) patients, and normative patients. In at least one embodiment, the kit comprises a specific amount (see exemplary amounts presented below, however, it should be appreciated by those skilled in the art are non-exhaustive and other amounts are also envisaged depending upon the patient to be treated or condition, disease, or disorder to be addressed) of the individual doses in a package containing a pharmaceutically effective amount of at least one conjugate of oxycodone of the present technology. The kit can further include instructions for use of the kit. The instructions can be directed to the use of said conjugate in a dosage range of between about 2 mg to about 200 mg per dose, including about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 128 mg, about 129 mg, about 130 mg, about 131 mg, about 132 mg, about 133 mg, about 134 mg, about 135 mg, about 136 mg, about 137 mg, about 138 mg, about 139 mg, about 140 mg, about 141 mg, about 142 mg, about 143 mg, about 144 mg, about 145 mg, about 146 mg, about 147 mg, about 148 mg, about 149 mg, about 150 mg, about 151 mg, about 152 mg, about 153 mg, about 154 mg, about 155 mg, about 156 mg, about 157 mg, about 158 mg, about 159 mg, about 160 mg, about 161 mg, about 162 mg, about 163 mg, about 164 mg, about 165 mg, about 166 mg, about 167 mg, about 168 mg, about 169 mg, about 170 mg, about 171 mg, about 172 mg, about 173 mg, about 174 mg, about 175 mg, about 176 mg, about 177 mg, about 178 mg, about 179 mg, about 180 mg, about 181 mg, about 182 mg, about 183 mg, about 184 mg, about 185 mg, about 186 mg, about 187 mg, about 188 mg, about 189 mg, about 190 mg, about 191 mg, about 191 mg, about 192 mg, about 193 mg, about 194 mg, about 195 mg, about 196 mg, about 197 mg, about 198 mg, about 199 mg, and about 200 mg per dose. The specified amount of individual doses may contain from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, 1, 2, 5, 10 and multiplied factors thereof, (e.g., ×2, ×2.5, ×5, ×10, ×100, etc).

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1: Oral PK Profiles of Conjugated Oxycodone of the Present Technology

Oral PK curves were determined for a number of prodrug conjugates of the present technology. Rats were orally administered at an amount of the conjugate equivalent to 2 mg/kg of freebase oxycodone and the plasma concentrations of released oxycodone were measured over time by LC-MS/MS. The results are tabulated in the following Tables 1, 2 and 3:

TABLE 1

Pharmacokinetic parameters of oxycodone released from the oxycodone conjugates after oral administration in rats

| Conjugate | AUC [ng/mL × h] | $C_{max}$ [ng/mL] | $t_{max}$ [h] | %-AUC of OC | %-$C_{max}$ of OC | %-$t_{max}$ of OC |
|---|---|---|---|---|---|---|
| 6-Ibu-OC | 77.9 | 39.5 | 0.44 | 83% | 62% | 47% |
| 6-Cinnamate-OC | 55.9 | 35.5 | 0.30 | 60% | 56% | 32% |
| 4-MeO-Bz-OC | 55.5 | 28.5 | 0.25 | 59% | 61% | 33% |
| 6-Fenoprofen-OC | 21.6 | 14.0 | 0.25 | 69% | 87% | 83% |
| 6-Ketoprofen-OC | 25.5 | 14.7 | 0.25 | 81% | 91% | 83% |
| 6-Tolfenamate-OC | 17.2 | 7.0 | 1.38 | 55% | 44% | 458% |
| 4-OH-Bz-OC | 53.5 | 35.4 | 0.75 | 58% | 69% | 188% |
| 3-ABz-OC | 52.9 | 45.5 | 0.55 | 83% | 96% | 122% |

Figure 14:
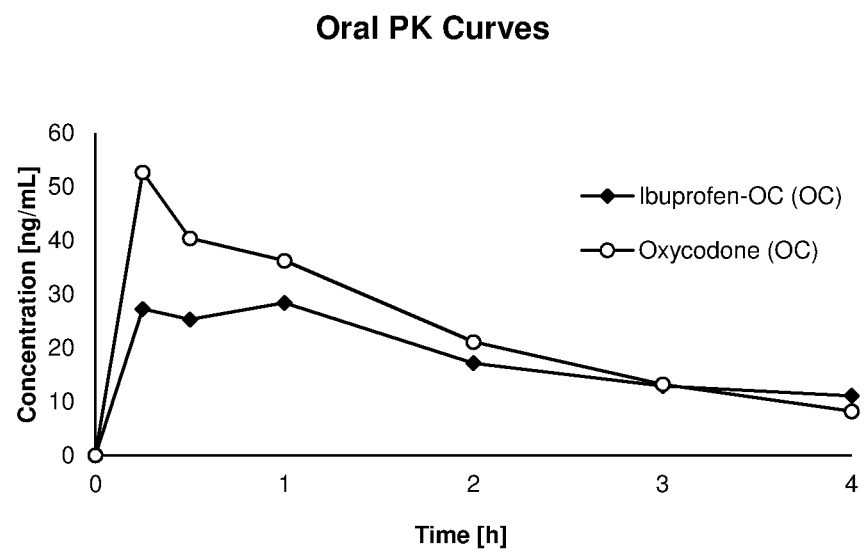
FIG. 14 provides PK profile graph information from an oral rat study comparing oxycodone plasma concentrations generated by oxycodone hydrochloride and Ibuprofen-OC.

OC: Oxycodone
AUC: Area Under the Curve
$C_{max}$: Peak plasma concentration
$t_{max}$: Time to peak plasma concentration The PK profile graphs from the oral rat study comparing oxycodone plasma concentrations generated by oxycodone hydrochloride and Ibuprofen-OC are shown in FIG. 14.

Figure 15:
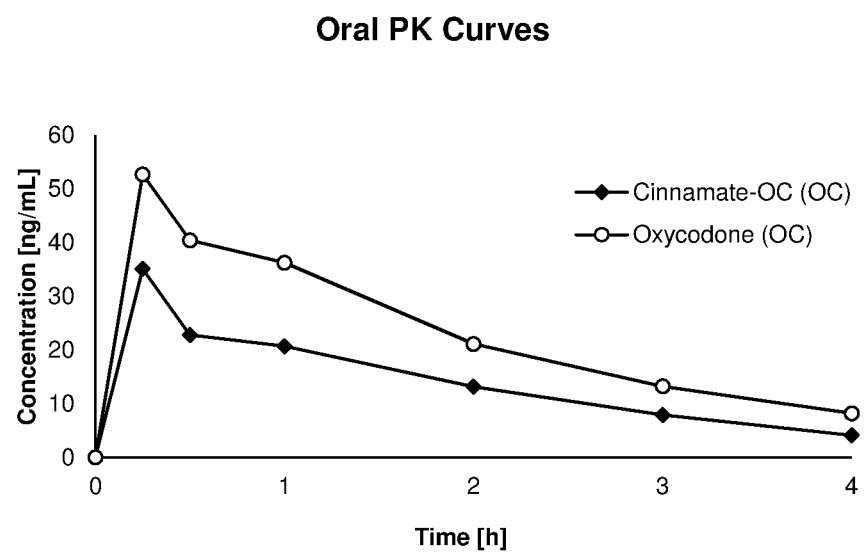
FIG. 15 provides PK profile graph data from an oral rat study comparing oxycodone plasma concentrations generated by oxycodone hydrochloride and Cinnamate-OC.

The PK profile graphs from the oral rat study comparing oxycodone plasma concentrations generated by oxycodone hydrochloride and Cinnamate-OC are shown in FIG. 15.

Figure 16:
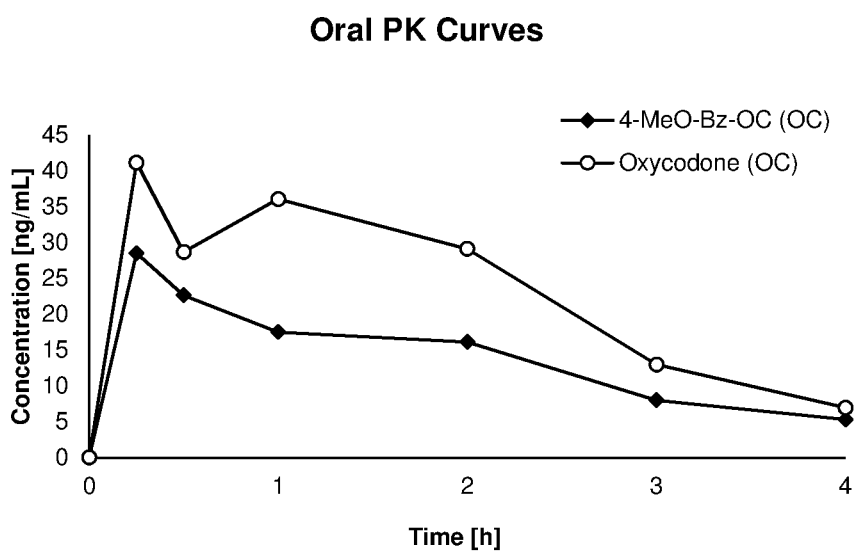
FIG. 16 provides PK profile graph data from an oral rat study comparing oxycodone plasma concentrations generated by oxycodone hydrochloride and 4-MeO-Bz-OC.

The PK profile graphs from the oral rat study comparing oxycodone plasma concentrations generated by oxycodone hydrochloride and 4-MeO-Bz-OC are shown in FIG. 16.

Figure 17:
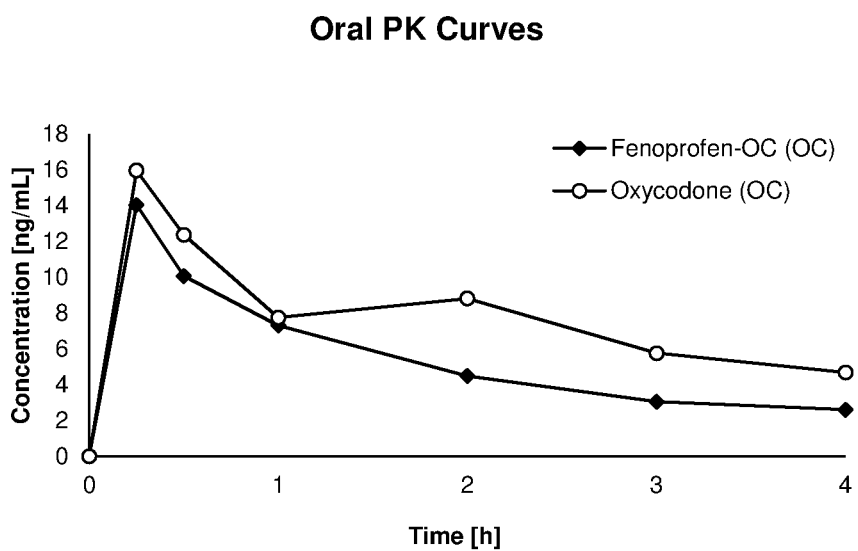
FIG. 17 provides PK profile graph data from an oral rat study comparing oxycodone plasma concentrations generated by oxycodone hydrochloride and Fenoprofen-OC.

The PK profile graphs from the oral rat study comparing oxycodone plasma concentrations generated by oxycodone hydrochloride and Fenoprofen-OC are shown in FIG. 17.

Figure 18:
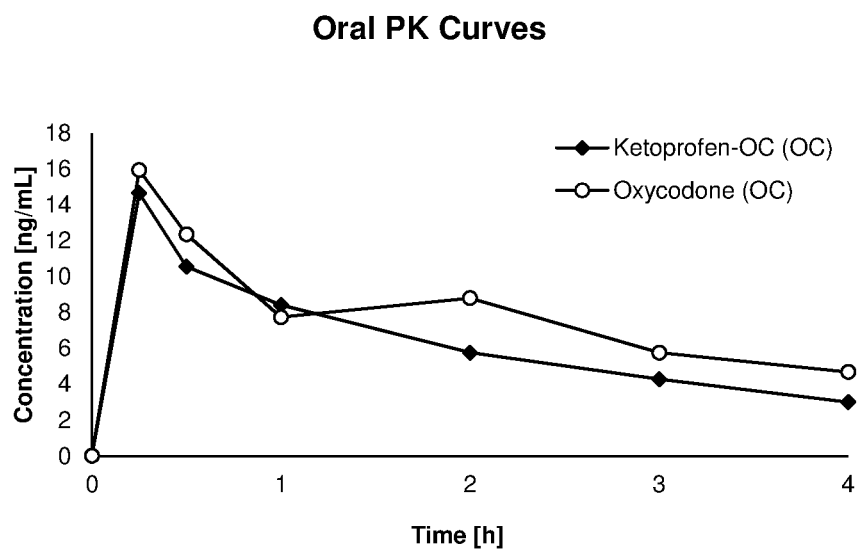
FIG. 18 provides PK profile graph data from an oral rat study comparing oxycodone plasma concentrations generated by oxycodone hydrochloride and Ketoprofen-OC.

The PK profile graphs from the oral rat study comparing oxycodone plasma concentrations generated by oxycodone hydrochloride and Ketoprofen-OC are shown in FIG. 18.

Figure 19:
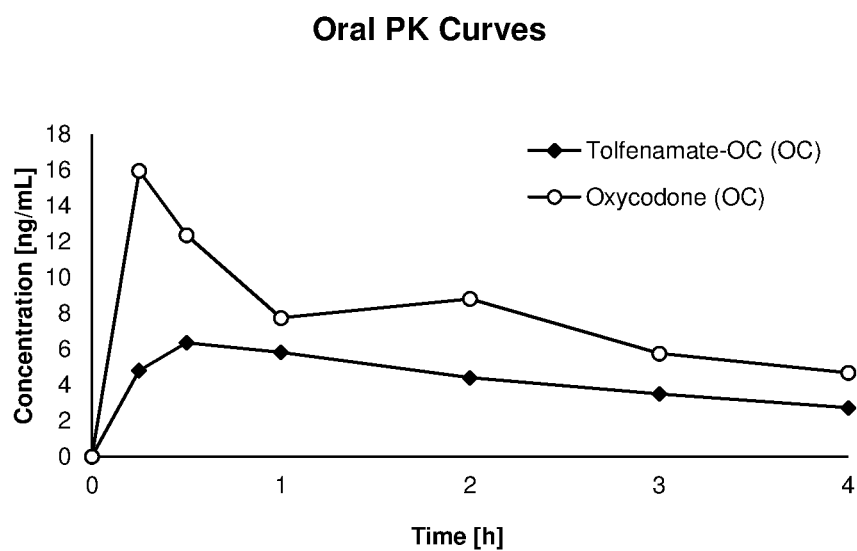
FIG. 19 provides PK profile graph data from an oral rat study comparing oxycodone plasma concentrations generated by oxycodone hydrochloride and Tolfenamate-OC.

The PK profile graphs from the oral rat study comparing oxycodone plasma concentrations generated by oxycodone hydrochloride and Tolfenamate-OC are shown in FIG. 19.

Figure 24:
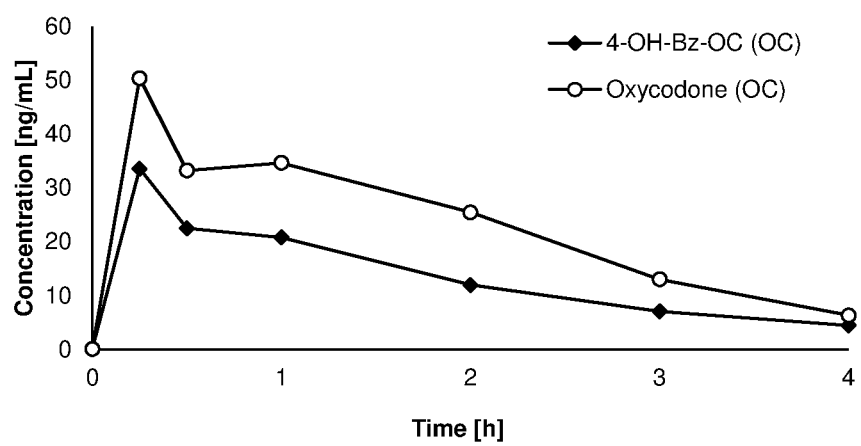
FIG. 24 provides PK profile graph data from an oral rat study comparing oxycodone plasma concentrations generated by oxycodone hydrochloride and 4-OH-Bz-OC.

The PK profile graphs from the oral rat study comparing oxycodone plasma concentrations generated by oxycodone hydrochloride and 4-OH-Bz-OC are shown in FIG. 24.

Figure 36:
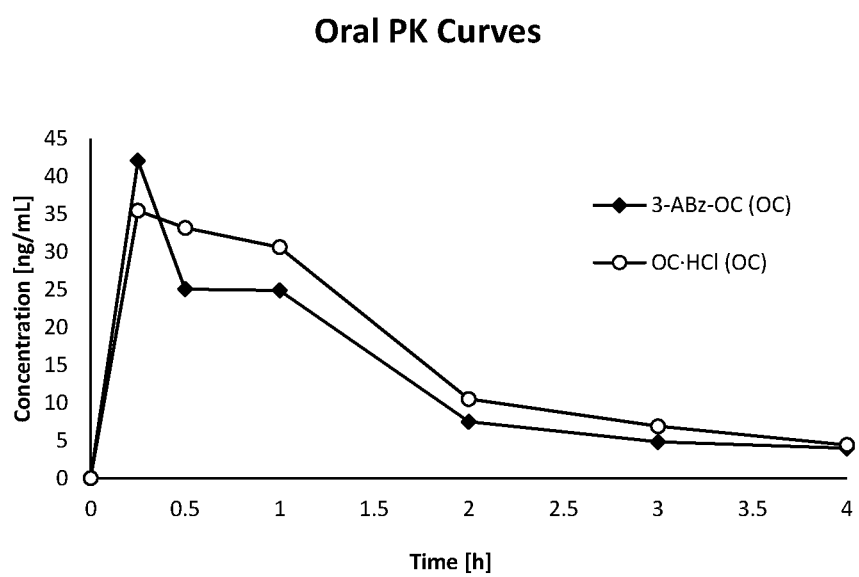
FIG. 36 provides PK profile graph data for an oral rat study comparing oxycodone plasma concentrations generated by oxycodone hydrochloride and 3-amino-Bz-OC.

The PK profile graphs from the oral rat study comparing oxycodone plasma concentrations generated by oxycodone hydrochloride and 4-Amino-Bz-OC are shown in FIG. 36.

Figure 25:
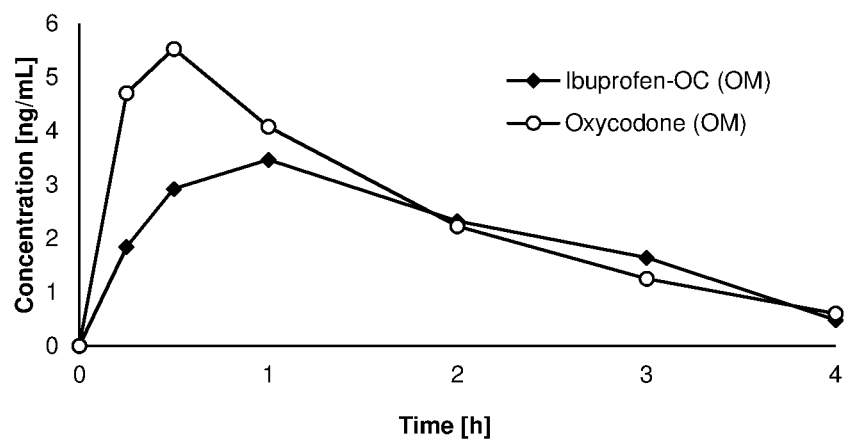
FIG. 25 provides PK profile graph data from an oral rat study comparing oxymorphone plasma concentrations generated by oxycodone hydrochloride and Ibuprofen-OC.

In other experiments, rats were orally administered an amount of a conjugate equivalent to 2 mg/kg of freebase oxycodone and the plasma concentrations of oxymorphone were measured over time by LC-MS/MS. The results are tabulated in the following Table 2:

The PK profile graphs from the oral rat study comparing oxymorphone plasma concentrations generated by oxycodone hydrochloride and Ibuprofen-OC are shown in FIG. 25.

Figure 26:
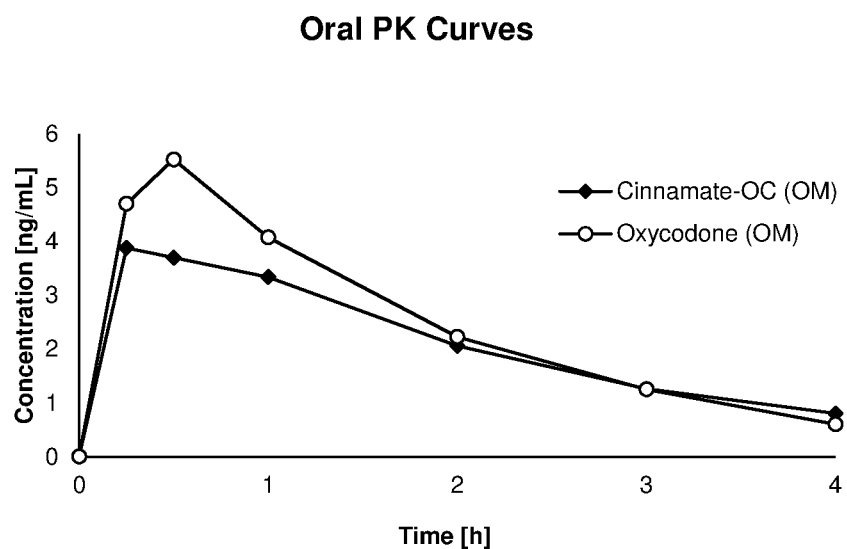
FIG. 26 provides PK profile graph data for an oral rat study comparing oxymorphone plasma concentrations generated by oxycodone hydrochloride and Cinnamate-OC.

The PK profile graphs from the oral rat study comparing oxymorphone plasma concentrations generated by oxycodone hydrochloride and Cinnamate-OC are shown in FIG. 26.

Figure 27:
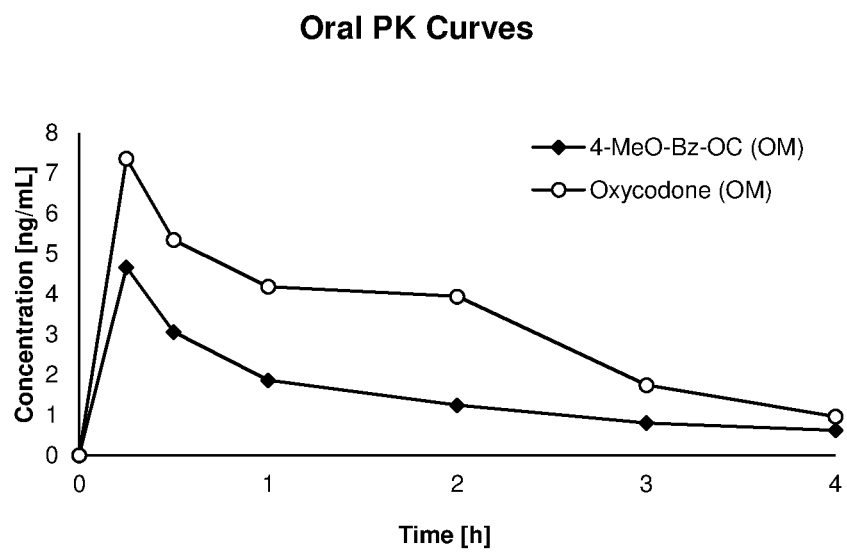
FIG. 27 provides PK profile graph data for an oral rat study comparing oxymorphone plasma concentrations generated by oxycodone hydrochloride and 4-MeO-Bz-OC.

The PK profile graphs from the oral rat study comparing oxymorphone plasma concentrations generated by oxycodone hydrochloride and 4-MeO-Bz-OC are shown in FIG. 27.

Figure 28:
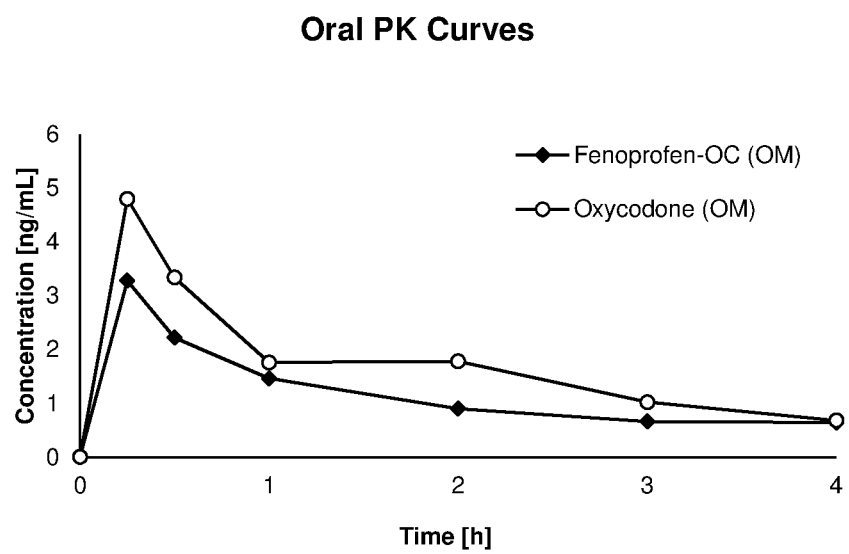
FIG. 28 provides PK profile graph data for an oral rat study comparing oxymorphone plasma concentrations generated by oxycodone hydrochloride and Fenoprofen-OC.

The PK profile graphs from the oral rat study comparing oxymorphone plasma concentrations generated by oxycodone hydrochloride and Fenoprofen-OC are shown in FIG. 28.

Figure 29:
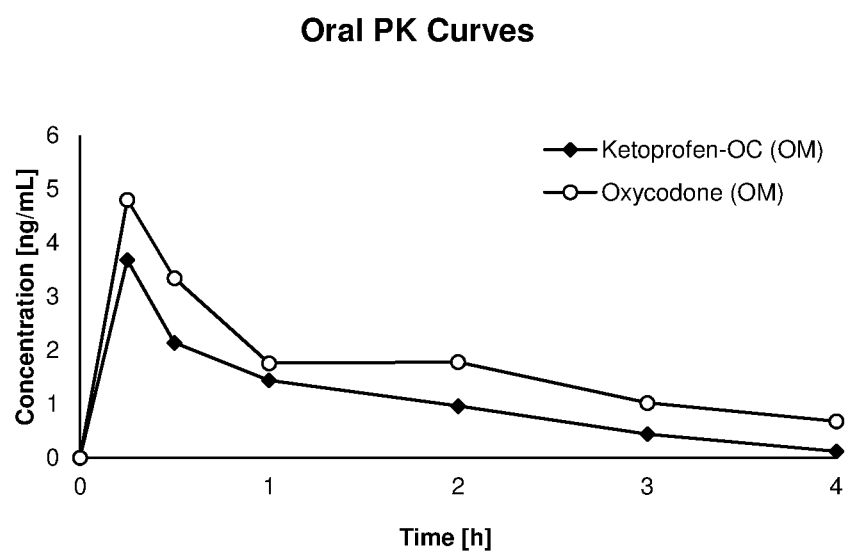
FIG. 29 provides PK profile graph data for an oral rat study comparing oxymorphone plasma concentrations generated by oxycodone hydrochloride and Ketoprofen-OC.

The PK profile graphs from the oral rat study comparing oxymorphone plasma concentrations generated by oxycodone hydrochloride and Ketoprofen-OC are shown in FIG. 29.

Figure 30:
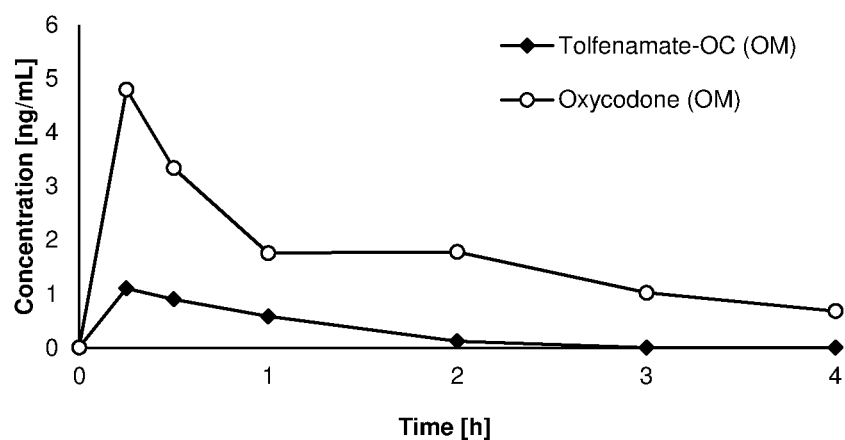
FIG. 30 provides PK profile graph data for an oral rat study comparing oxymorphone plasma concentrations generated by oxycodone hydrochloride and Tolfenamate-OC.

The PK profile graphs from the oral rat study comparing oxymorphone plasma concentrations generated by oxycodone hydrochloride and Tolfenamate-OC are shown in FIG. 30.

Figure 31:
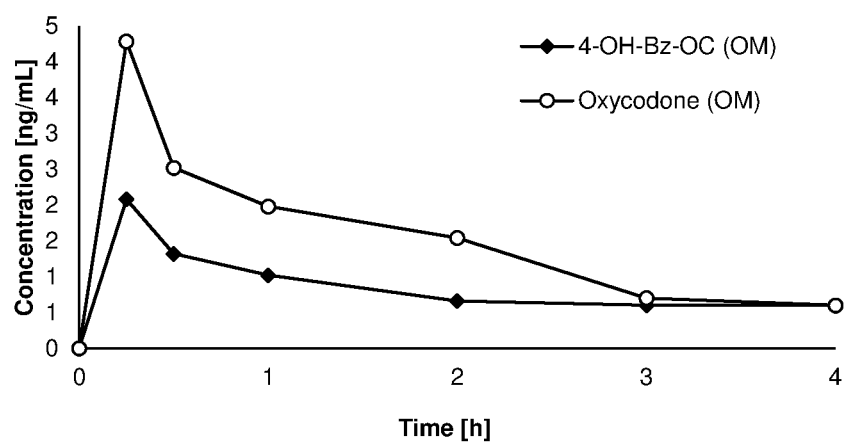
FIG. 31 provides PK profile graph data for an oral rat study comparing oxymorphone plasma concentrations generated by oxycodone hydrochloride and 4-OH-Bz-OC.

The PK profile graphs from the oral rat study comparing oxymorphone plasma concentrations generated by oxycodone hydrochloride and 4-OH-Bz-OC are shown in FIG. 31.

Figure 37:
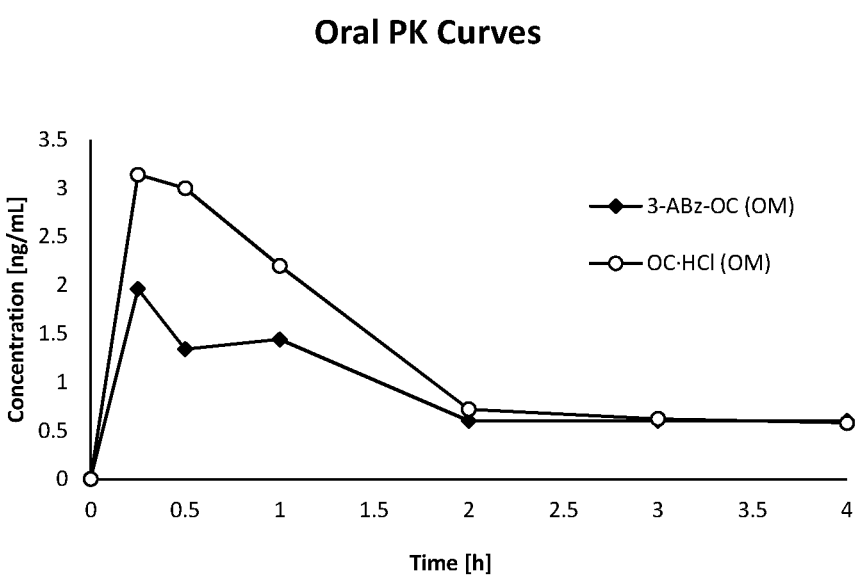
FIG. 37 provides PK profile graph data for an oral rat study comparing oxymorphone plasma concentrations generated by oxycodone hydrochloride and 3-amino-Bz-OC.

The PK profile graphs from the oral rat study comparing oxymorphone plasma concentrations generated by 3-Amino-Bz-OC and OC Hydrochloride are shown in FIG. 37.

TABLE 2

PK parameters of oxymorphone released from the oxycodone conjugates after oral administration in rats

| Conjugate | AUC [ng/mL × h] | $C_{max}$ [ng/mL] | $t_{max}$ [h] | %-AUC of OC | %-$C_{max}$ of OC | %-$t_{max}$ of OC |
|---|---|---|---|---|---|---|
| 6-Ibu-OC | 8.4 | 3.7 | 1.15 | 83% | 59% | 131% |
| 6-Cinnamate-OC | 9.2 | 4.3 | 0.35 | 91% | 68% | 40% |
| 4-MeO-Bz-OC | 6.7 | 4.7 | 0.25 | 51% | 63% | 83% |
| 6-Fenoprofen-OC | 4.6 | 3.3 | 0.25 | 67% | 68% | 100% |
| 6-Ketoprofen-OC | 4.3 | 3.7 | 0.25 | 62% | 77% | 100% |
| 6-Tolfenamate-OC | 1.2 | 1.3 | 0.31 | 17% | 26% | 125% |
| 4-OH-Bz-OC | 3.3 | 2.1 | 0.25 | 55% | 49% | 100% |
| 3-ABz-OC | 3.6 | 2.0 | 0.44 | 69% | 49% | 97% |

Example 2: Intranasal PK Profiles of Conjugated Oxycodone of the Present Technology Intranasal PK curves were determined for a number of prodrug conjugates of the present technology. Rats were intranasally administered at an amount of the conjugate equivalent to 2 mg/kg of freebase oxycodone and the plasma concentrations of released oxycodone were measured over time by LC-MS/MS. The results are tabulated in the following Tables 4 and 5:

TABLE 4

PK parameters of oxymorphone released from the oxycodone conjugates after intranasal administration in rats

| Conjugate | AUC [ng/mL × h] | $C_{max}$ [ng/mL] | $t_{max}$ [h] | %-AUC of OC | %-$C_{max}$ of OC | %-$t_{max}$ of OC |
|---|---|---|---|---|---|---|
| 6-Ibu-OC | 81.6 | 131.7 | 0.083 | 23% | 10% | 100% |
| 6-Cinnamate-OC | 225.0 | 497.2 | 0.083 | 39% | 22% | 100% |
| 4-MeO-Bz-OC | 372.9 | 949.4 | 0.083 | 68% | 48% | 100% |
| 4-OH-Bz-OC | 339.9 | 759.2 | 0.083 | 58% | 41% | 100% |

Figure 20:
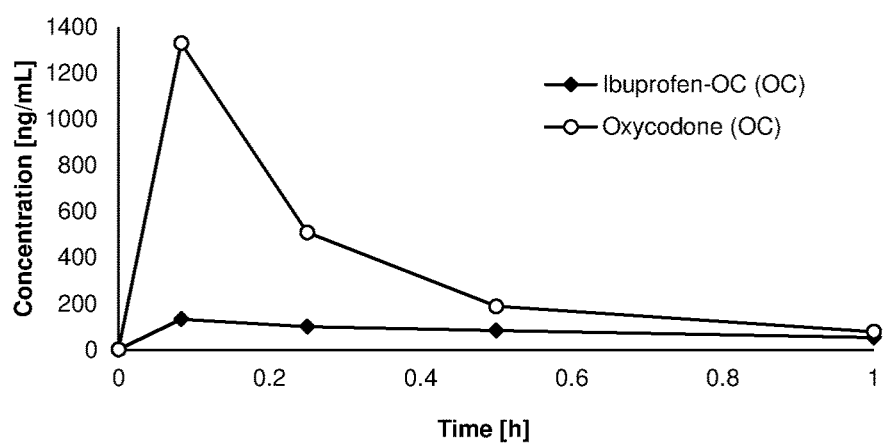
FIG. 20 provides PK profile graph data from an intranasal rat study comparing oxycodone plasma concentrations generated by oxycodone hydrochloride and Ibuprofen-OC.

The PK profile graphs from the intranasal rat study comparing oxycodone plasma concentrations generated by oxycodone hydrochloride and Ibuprofen-OC are shown in FIG. 20.

Figure 21:
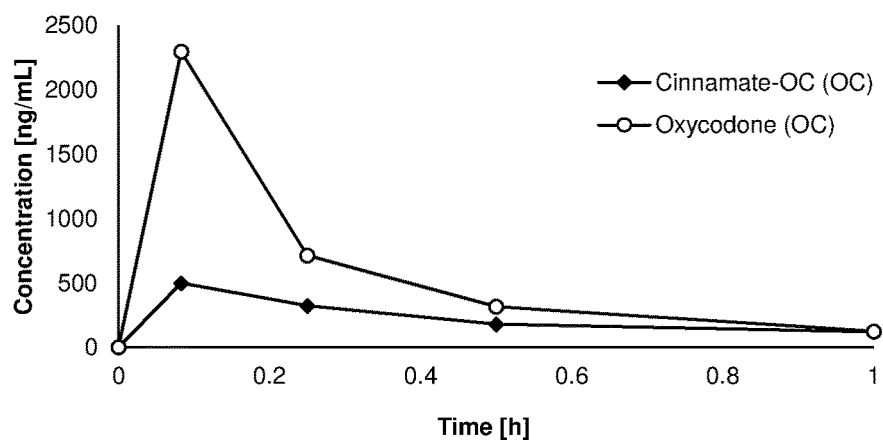
FIG. 21 provides PK profile graph data from an intranasal rat study comparing oxycodone plasma concentrations generated by oxycodone hydrochloride and Cinnamate-OC.

The PK profile graphs from the intranasal rat study comparing oxycodone plasma concentrations generated by oxycodone hydrochloride and Cinnamate-OC are shown in FIG. 21.

Figure 22:
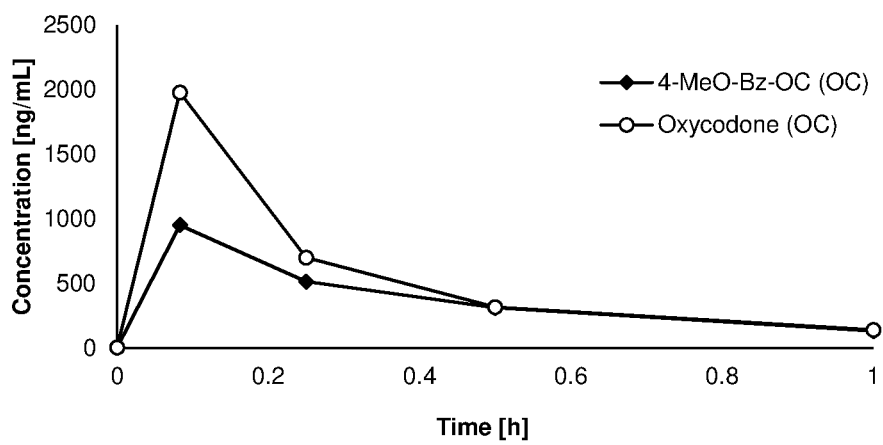
FIG. 22 provides PK profile graph data from an intranasal rat study comparing oxycodone plasma concentrations generated by oxycodone hydrochloride and 4-MeO-Bz-OC.

The PK profile graphs from the intranasal rat study comparing oxycodone plasma concentrations generated by oxycodone hydrochloride and 4-MeO-Bz-OC are shown in FIG. 22.

Figure 23:
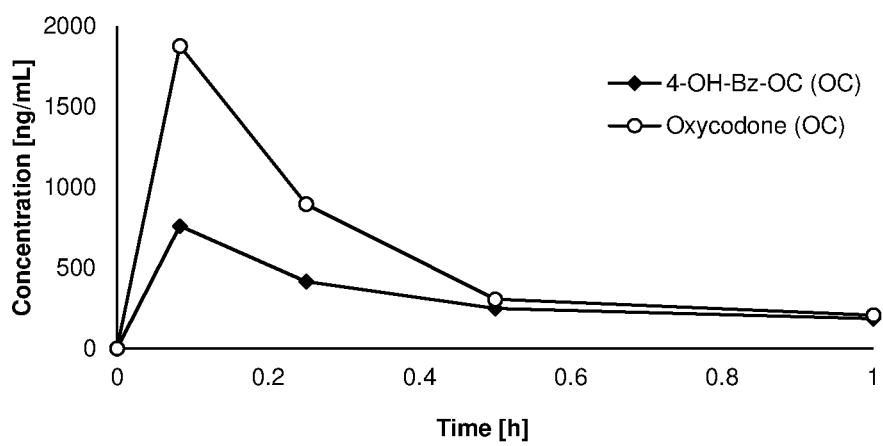
FIG. 23 provides PK profile graph data from an intranasal rat study comparing oxycodone plasma concentrations generated by oxycodone hydrochloride and 4-OH-Bz-OC.

The PK profile graphs from the intranasal rat study comparing oxycodone plasma concentrations generated by oxycodone hydrochloride and 4-OH-Bz-OC are shown in FIG. 23.

In other experiments, rats were intranasally administered an amount of the conjugate equivalent to 2 mg/kg of freebase oxycodone and the plasma concentrations of released oxymorphone were measured over time by LC-MS/MS. The results are tabulated in the following Table 6:

TABLE 6

PK parameters of oxymorphone released from the oxycodone conjugates after intranasal administration in rats

| Conjugate | AUC [ng/mL × h] | $C_{max}$ [ng/mL] | $t_{max}$ [h] | %-AUC of OC | %-$C_{max}$ of OC | %-$t_{max}$ of OC |
|---|---|---|---|---|---|---|
| 6-Ibu-OC | 0.7 | 1.0 | 0.500 | 11% | 11% | 143% |
| 6-Cinnamate-OC | 1.7 | 2.4 | 0.500 | 18% | 18% | 133% |
| 4-MeO-Bz-OC | 7.2 | 9.4 | 0.367 | 65% | 60% | 105% |
| 4-OH-Bz-OC | 11.8 | 19.0 | 0.450 | 58% | 61% | 90% |

Figure 32:
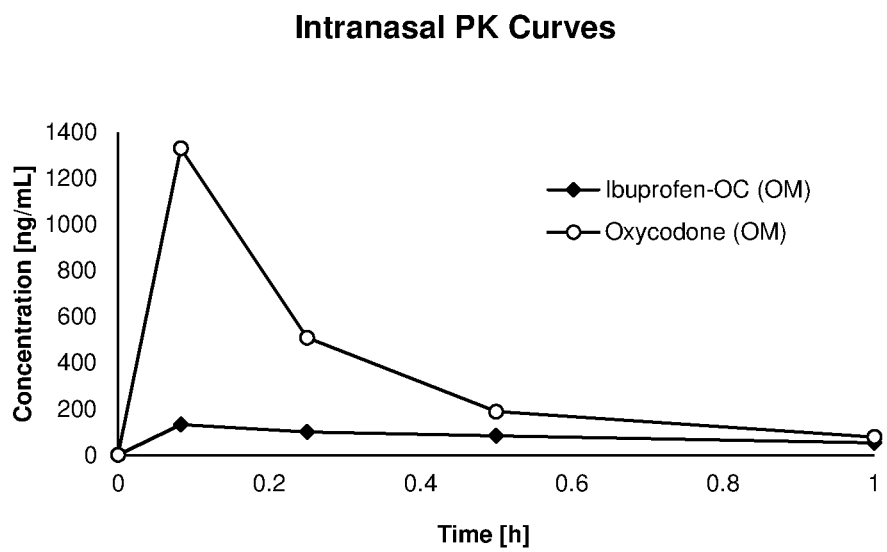
FIG. 32 provides PK profile graph data for an intranasal rat study comparing oxymorphone plasma concentrations generated by oxycodone hydrochloride and Ibuprofen-OC.

The PK profile graphs from the intranasal rat study comparing oxymorphone plasma concentrations generated by oxycodone hydrochloride and Ibuprofen-OC are shown in FIG. 32.

Figure 33:
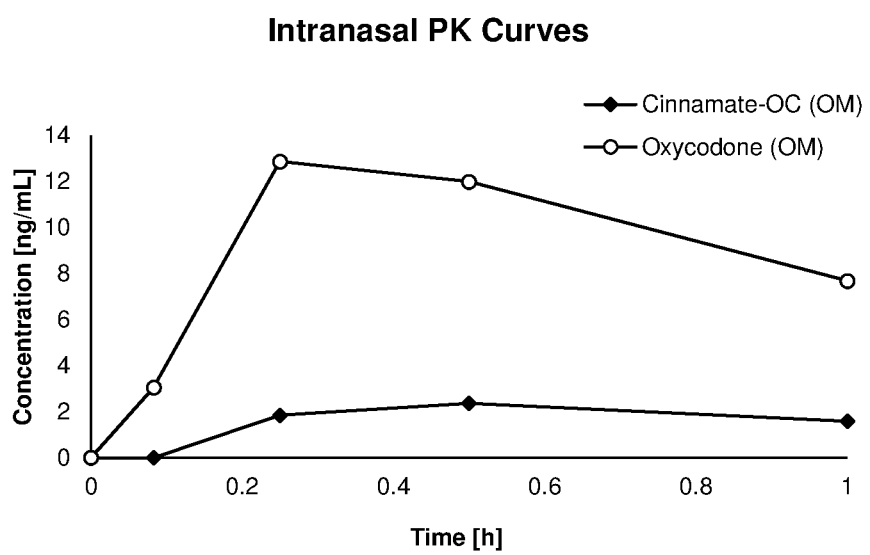
FIG. 33 provides PK profile graph data for an intranasal rat study comparing oxymorphone plasma concentrations generated by oxycodone hydrochloride and Cinnamate-OC.

The PK profile graphs from the intranasal rat study comparing oxymorphone plasma concentrations generated by oxycodone hydrochloride and Cinnamate-OC are shown in FIG. 33.

Figure 34:
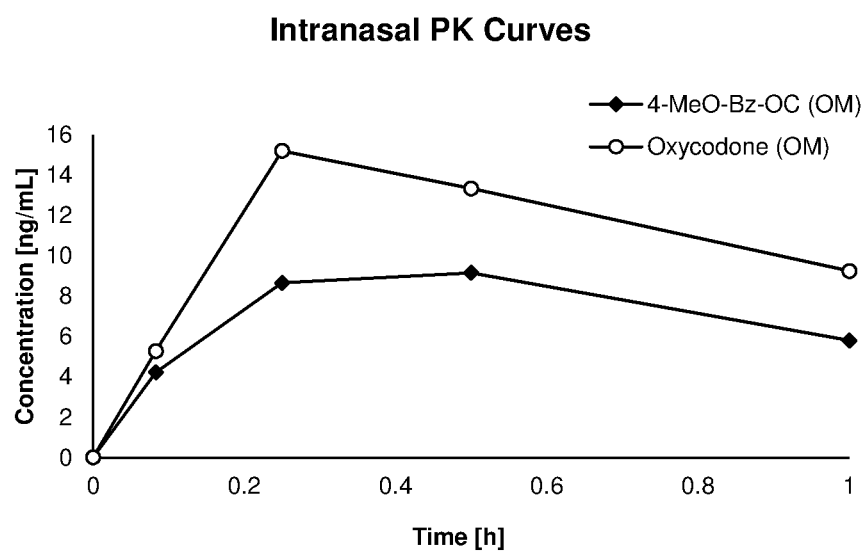
FIG. 34 provides PK profile graph data for an intranasal rat study comparing oxymorphone plasma concentrations generated by oxycodone hydrochloride and 4-MeO-Bz-OC.

The PK profile graphs from the intranasal rat study comparing oxymorphone plasma concentrations generated by oxycodone hydrochloride and 4-MeO-Bz-OC are shown in FIG. 34.

Figure 35:
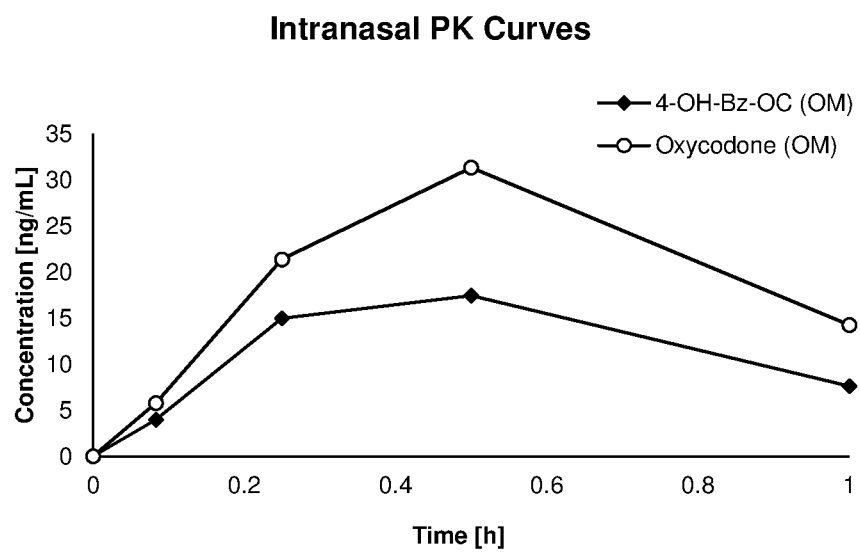
FIG. 35 provides PK profile graph data for an intranasal rat study comparing oxymorphone plasma concentrations generated by oxycodone hydrochloride and 4-OH-Bz-OC.

The PK profile graphs from the intranasal rat study comparing oxymorphone plasma concentrations generated by oxycodone hydrochloride and 4-OH-Bz-OC are shown in FIG. 35.

Example 3: Tamper Resistance

Effective abuse deterrent forms of drugs of abuse can also be resistant to chemical tampering. The prodrugs in the present technology also impart this characteristic. Several common tampering scenarios were employed and percent of OC released were determined by liquid chromatography with tandem mass spectrometry (LC-MS/MS). The results as shown in Table 7 indicated a very high degree of tamper resistance in the example OC prodrugs, releasing little to no OC.

Example 4: Comparison Tests

The presently claimed technology utilizes covalent conjugation of an opioid, oxycodone, with various aryl carboxylic acids to reduce the potential for causing overdose or abuse by requiring the active pharmaceutical ingredient (API), oxycodone, to be released in vivo after oral administration. These conjugates are intended to be prodrugs of the known-safe, but highly abused, parent molecules. To fulfill the generally accepted definition of a prodrug, the conjugate cannot have significant pharmacological activity and only become effective after release of the active moiety in vivo.

The presently described technology relates to oxycodone conjugates that may appear structurally similar to examples in previously described technologies but their properties are profoundly different and not obvious. To illustrate this, the oral pharmacokinetic (PK) profiles of some of the presently claimed conjugates of oxycodone are plotted against structurally similar conjugates of hydrocodone, hydromorphone and oxymorphone.

The plasma concentration measurement of each opioid released from a conjugate was normalized to the corresponding maximum plasma concentration ($C_{max}$) of its parent opioid at an equimolar dose (i.e., $C_{max}$ of the parent opioid was set to 100%). The resulting PK curves show plasma concentrations of the opioids released from various conjugates plotted as percent of peak plasma concentration ($C_{max}$)

of each respective parent opioid. This facilitates the comparison of the opioid concentrations produced by several conjugates of different opioids conjugated with the same carboxylic acid.

Figure 38:
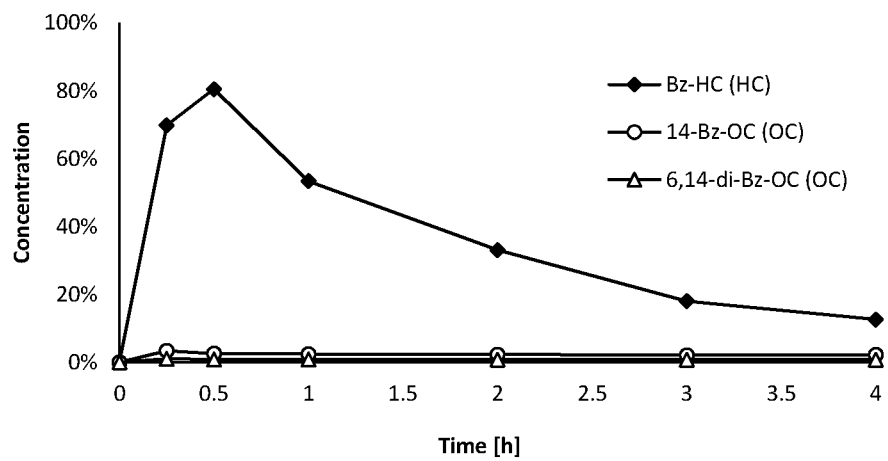
FIG. 38 provides PK profile graph data for an oral rat study comparing plasma concentrations generated by Bz-HC, 14-Bz-oxycodone and 6,14-di-Bz-OC.

For example, FIG. 38 compares two benzoic acid conjugates of oxycodone with a similar conjugate of hydrocodone. While the hydrocodone conjugate produced similar released opioid plasma concentrations as its parent opioid (hydrocodone bitartrate), both oxycodone conjugates exhibited blunted released opioid plasma concentrations compared to their parent opioid (oxycodone hydrochloride).

Figure 39:
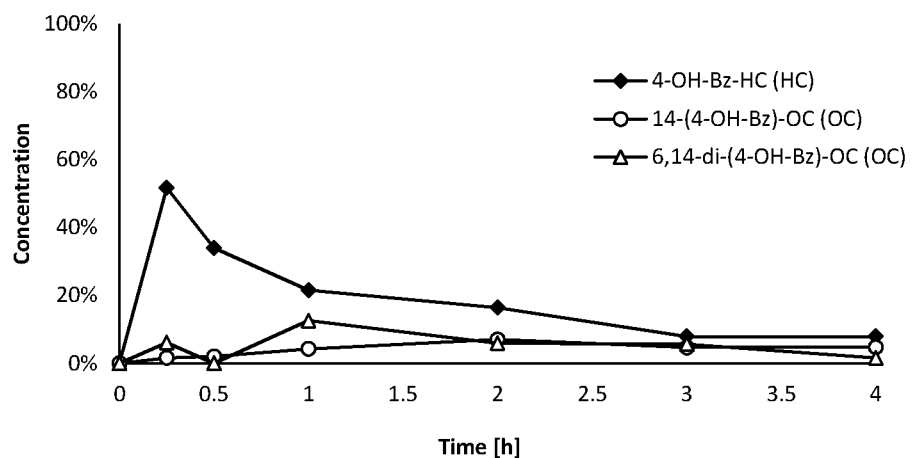
FIG. 39 provides PK profile graph data for an oral rat study comparing plasma concentrations generated by 6,14-di-(4-OH-Bz)-OC, 14-(4-OH-Bz)-OC and 4-OH-Bz-HC.

FIG. 39 compares two oxycodone prodrugs conjugated with 4-hydroxy-benzoic acid to one hydrocodone conjugated with the same acid. In this example, the hydrocodone conjugate exhibited a higher opioid release compared to both oxycodone conjugates despite hydrocodone being covalently bound to the same acid as the oxycodone conjugates. Interestingly, the oxycodone conjugates had similar bioavailability despite one of the conjugates comprising two 4-hydroxy-benzoic acid molecules and the other only one.

Figure 40:
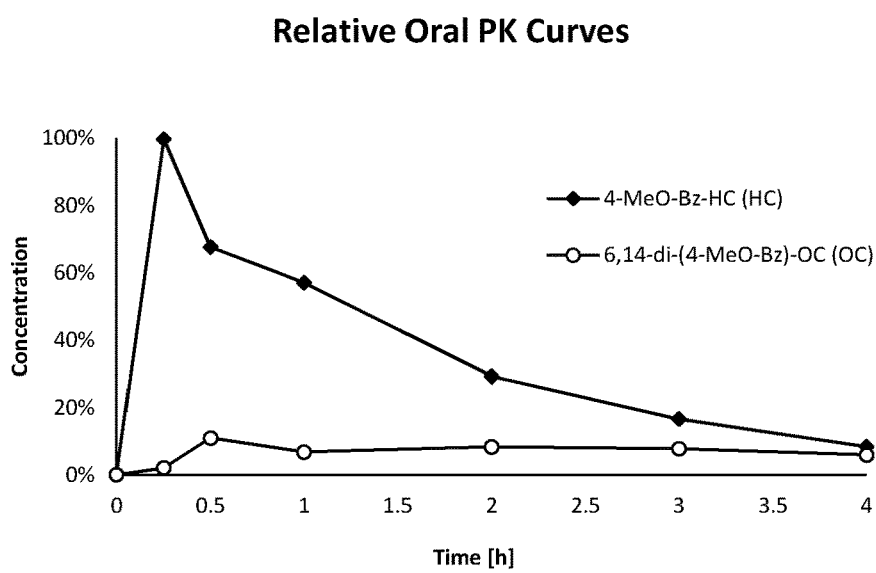
FIG. 40 provides PK profile graph data for an oral rat study comparing plasma concentrations generated by 4-MeO-Bz-HC and 6,14-di-(4-MeO-Bz)-OC.

FIG. 40 shows the relative PK profiles of 4-methoxybenzoic acid conjugates of oxycodone and hydrocodone. Again, the release profiles of the two different opioids were very different and unexpected.

Figure 41:
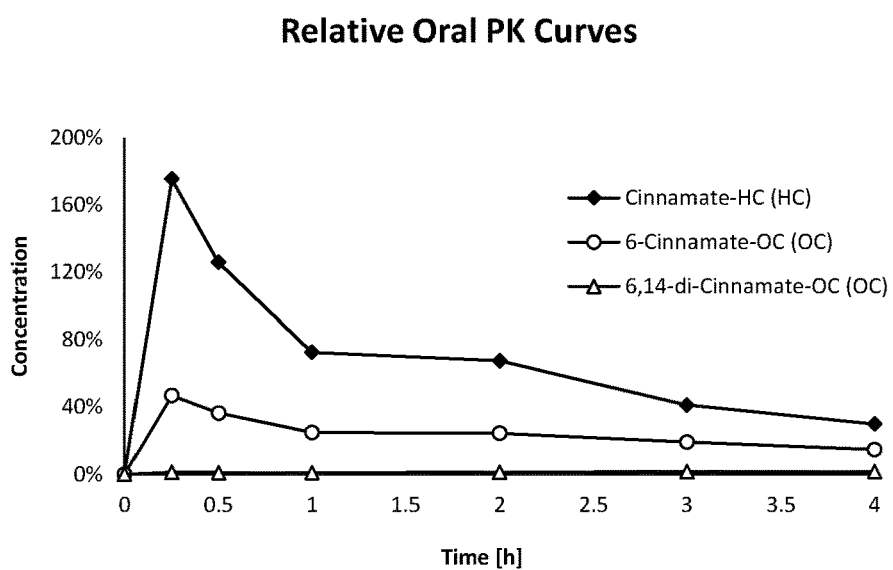
FIG. 41 provides PK profile graph data for an oral rat study comparing plasma concentrations generated by Cinnamate-HC, 6-Cinnamate-OC and 6,14-di-Cinnamate-OC.

FIG. 41 illustrates the PK profiles of cinnamic acid conjugated oxycodone and hydrocodone. Despite having identical cinnamic acid groups attached, the hydrocodone conjugate released more opioid compared to the oxycodone conjugates. The oxycodone prodrug with a single conjugated cinnamic acid molecule exhibited significantly higher oxycodone release compared to the oxycodone prodrug with two cinnamic acid molecules.

Figure 42:
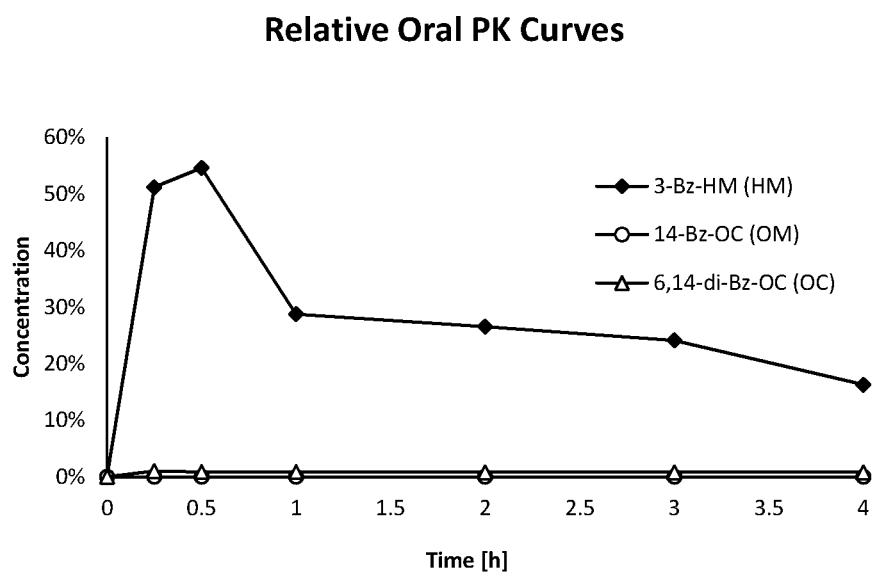
FIG. 42 provides PK profile graph data for an oral rat study comparing plasma concentrations generated by 14-Bz-OC, 6,14-di-Bz-OC and 3-Bz-HM.
Figure 43:
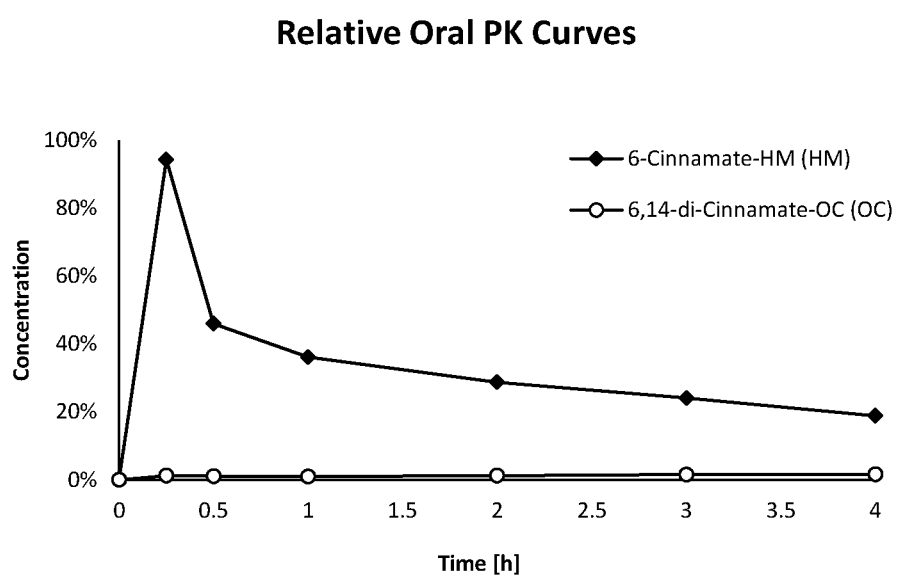
FIG. 43 provides PK profile graph data for an oral rat study comparing plasma concentrations generated by 6,14-di-Cinnamate-HM, and 6-Cinnamate-HM.
Figure 44:
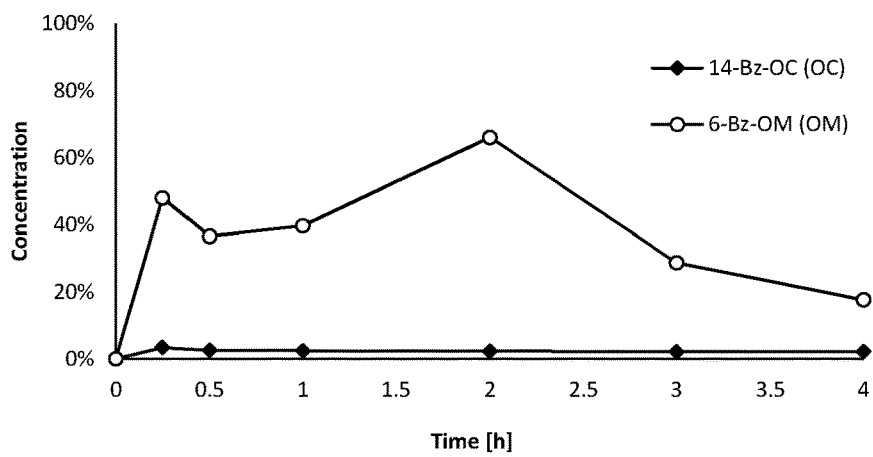
FIG. 44 provides PK profile graph data for an oral rat study comparing plasma concentrations generated by 14-Bz-OC, and 6-Bz-OM.
Figure 45:
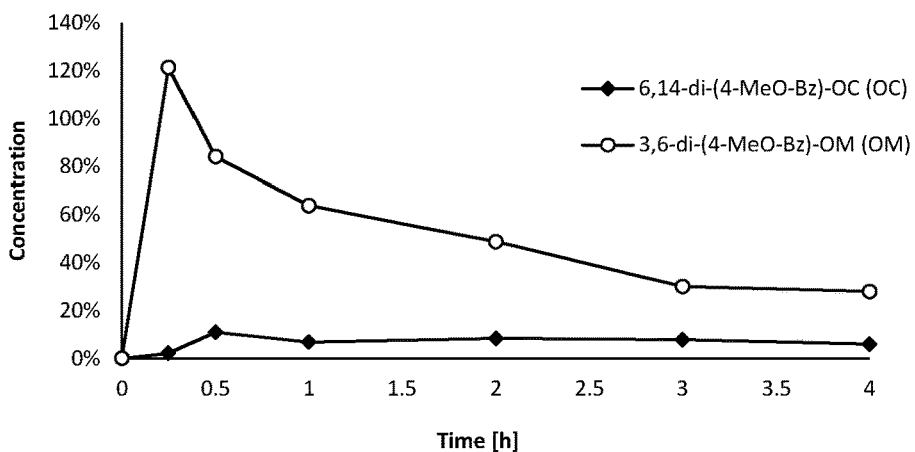
FIG. 45 provides PK profile graph data for an oral rat study comparing plasma concentrations generated by 6,14-di-(4-MeO-Bz)-OC and 3,6-di-(4-MeO-Bz)-OM.
Figure 46:
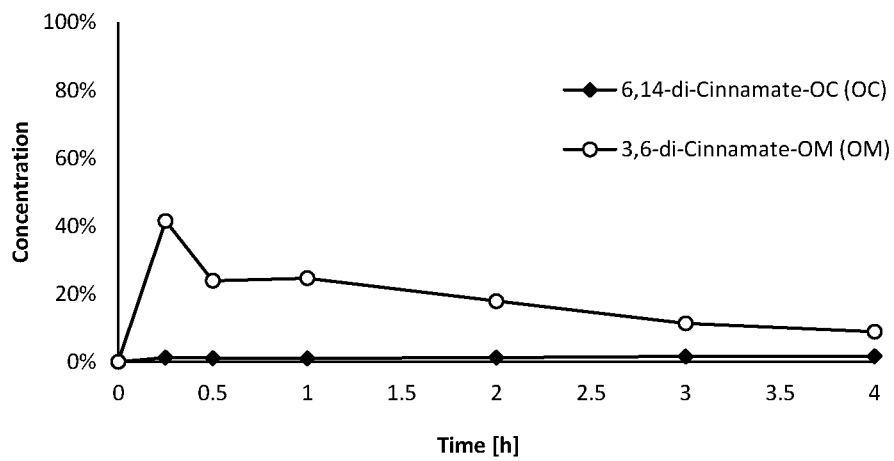
FIG. 46 provides PK profile graph data for an oral rat study comparing plasma concentrations generated by 6,14-di-Cinnamate-OC and 3,6-di-Cinnamate-OM.
Figure 47:
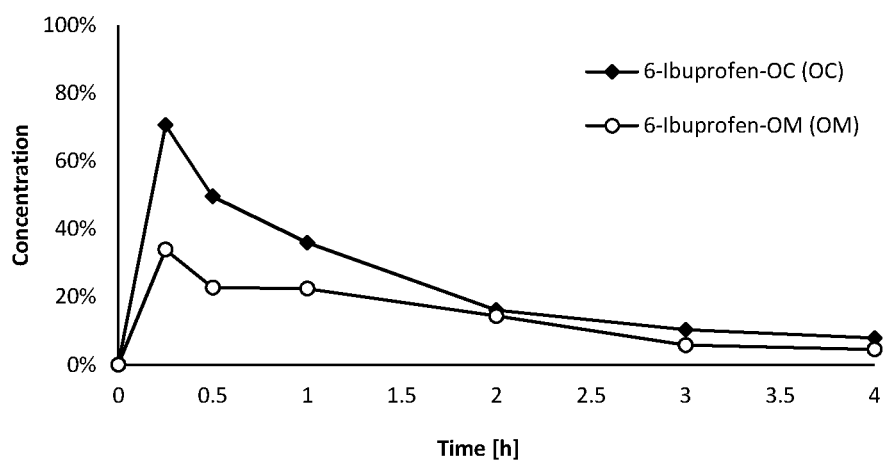
FIG. 47 provides PK profile graph data for an oral rat study comparing plasma concentrations generated by 6-ibuprofen-OC and 6-ibuprofen-OM.

Similarly, FIGS. 42 and 43 compared oxycodone prodrugs with hydromorphone prodrugs, FIGS. 44 through 45 compared oxycodone prodrugs with oxymorphone prodrugs and FIGS. 46 through 47 compared oxycodone prodrugs with oxymorphone prodrugs.

The PK profile data graphs from the presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

TABLE 7

Tamper resistant properties of various examples of oxycodone prodrugs.

| | Tampering Conditions | | | |
|---|---|---|---|---|
| | Water RT | | 1N HCl RT | 5% Bicarbonate RT |
| Time (hours) | 1 | 24 | 1 | 1 |
| Bz-OC | 0% | 0% | 0% | 0% |
| (4-OH-Bz)2-OC | 0% | 0% | 0% | 0% |
| (3-ABz)2-OC | 0% | 0% | 0% | 0% |
| (3-OH-Bz)2-OC | 0% | 0% | 0% | 0% |
| (Bz)2-OC | 0% | 0% | 0% | 0% |
| (4-MeO-Bz)2-OC | 0% | 0% | 0% | 0% |
| (4-OH-3-MeO-Bz)2-OC | 0% | 0% | 0% | 0% |
| 2-ABz-OC | <1% | <1% | 0% | 3% |
| (Cin)2-OC | 0% | 0% | 0% | 0% |
| 4-MeO-Bz-OC | 0% | <1% | <1% | <1% |
| 2-OH-Bz-OC | 0% | 0% | 0% | 5% |
| 4-OH-Bz-OC | 0% | 0% | 0% | 0% |
| 3-Abz-OC | 0% | 0% | <1% | <1% |
| Naprox-OC | 0% | 0% | <1% | 0% |
| 4-OH-3-MeO-Bz-OC | 0% | 0% | 0% | 0% |
| 3-OH-Bz-OC | 0% | 0% | <1% | 0% |

TABLE 7-continued

Tamper resistant properties of various examples of oxycodone prodrugs.

| | Tampering Conditions | | | |
|---|---|---|---|---|
| | Water RT | | 1N HCl RT | 5% Bicarbonate RT |
| Time (hours) | 1 | 24 | 1 | 1 |
| Ketopr-OC | 0% | <1% | 2% | 3% |
| Ibu-OC | 0% | 0% | 2% | 2% |
| Cin-OC | 0% | 0% | 0% | <1% |

RT = room temperature

The invention claimed is:

1. A composition comprising an oxycodone conjugate wherein the oxycodone is conjugated to 4-hydroxy-benzoic acid, pharmaceutically acceptable salt thereof, or a combination thereof, wherein the oxycodone conjugate has the following structural formula

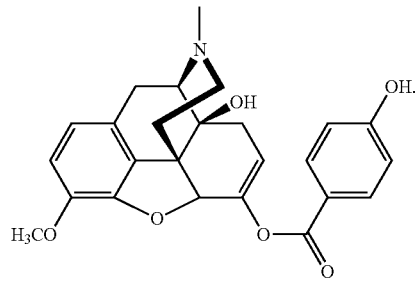

2. The composition of claim 1, wherein the oxycodone conjugate exhibits an improved AUC and rate of release over time when compared to unconjugated oxycodone over the same time period; exhibits less variability in the oral PK profile when compared to unconjugated oxycodone; or has reduced side effects when compared with unconjugated oxycodone.

3. The composition of claim 2, wherein the reduced side effects comprise reduced opioid induced constipation.

4. The composition of claim 1, wherein the composition is formulated for oral administration.

5. The composition of claim 4, wherein the composition formulated for oral administration is a tablet, capsule, caplet, pill, powder, troche, lozenge, slurry, liquid solution, suspension, emulsion, elixir or oral thin film (OTF).

6. The composition of claim 1, wherein the composition in a solid form, a solution, a suspension, or a soft gel form.

7. The composition of claim 6, wherein the solid form further comprises excipients, binders, derivatives thereof, or combinations thereof.

8. The composition of claim 7, wherein the binder is povidone.

9. The composition of claim 1, wherein the oxycodone conjugate is in an amount sufficient to provide a therapeutically equivalent AUC when compared to unconjugated oxycodone after oral administration.

10. The composition of claim 1, wherein the oxycodone conjugate is in an amount sufficient to provide a therapeutically equivalent AUC and $C_{max}$ when compared to an equivalent molar amount of unconjugated oxycodone after oral administration.

11. The composition of claim 1, wherein the oxycodone conjugate is in an amount sufficient to provide a therapeutically equivalent AUC and a lower $C_{max}$ when compared to an equivalent molar amount of unconjugated oxycodone after oral administration.

12. The composition of claim 1, wherein intranasal or intravenous administration of the oxycodone conjugate provides a lower AUC and/or $C_{max}$ when compared to an equivalent molar amount of unconjugated oxycodone.

13. The composition of claim 1, wherein oral administration of the oxycodone conjugate provides a decreased overdose potential when compared to an equivalent molar amount of unconjugated oxycodone.

14. The composition of claim 1, wherein the oxycodone conjugate provides an increased tamper resistance when compared to unconjugated oxycodone.

15. The composition of claim 1, wherein the pharmaceutically acceptable salt of the oxycodone conjugate is selected from the group consisting of an acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminium, lithium, cholinate, lysinium, ammonium, tromethamine, and derivatives thereof.

16. The composition of claim 1, wherein the oxycodone conjugate is present in an amount per unit dose of between about 1 mg and about 200 mg per unit dose wherein the amount per unit dose is based on the content of oxycodone.

17. A compound having the following structure

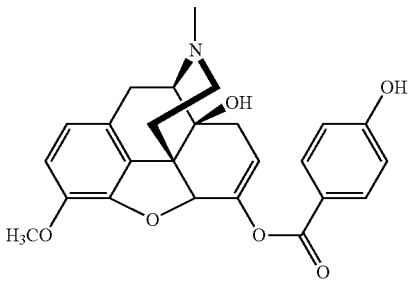

or a pharmaceutically acceptable salt thereof.

* * * * *